US008415453B2

(12) United States Patent
Wu et al.

(10) Patent No.: US 8,415,453 B2
(45) Date of Patent: Apr. 9, 2013

(54) LUNG CANCER-TARGETED PEPTIDES AND APPLICATIONS THEREOF

(75) Inventors: Han-Chung Wu, Taipei (TW); Chin-Tarng Lin, Taipei (TW); De-Kuan Chang, Taipei (TW)

(73) Assignees: Academia Sinica, Taipei (TW); National Taiwan University, Taipei (TW)

( * ) Notice: Subject to any disclaimer, the term of this patent is extended or adjusted under 35 U.S.C. 154(b) by 1398 days.

(21) Appl. No.: 11/783,927

(22) Filed: Apr. 13, 2007

(65) Prior Publication Data

US 2008/0193375 A1    Aug. 14, 2008

Related U.S. Application Data

(60) Provisional application No. 60/900,973, filed on Feb. 13, 2007, provisional application No. 60/901,085, filed on Feb. 14, 2007.

(51) Int. Cl.
*A61K 38/04*   (2006.01)
*A61K 9/127*   (2006.01)
*A61P 35/00*   (2006.01)

(52) U.S. Cl.
USPC ............................ 530/327; 514/19.3; 424/450

(58) Field of Classification Search ........................ None
See application file for complete search history.

(56) References Cited

U.S. PATENT DOCUMENTS

| | | | |
|---|---|---|---|
| 4,179,337 A | 12/1979 | Davis | |
| 4,301,144 A | 11/1981 | Iwashita | |
| 4,496,689 A | 1/1985 | Mitra | |
| 4,640,835 A | 2/1987 | Shimizu | |
| 4,670,417 A | 6/1987 | Iwasaki | |
| 4,791,192 A | 12/1988 | Nakagawa | |
| 5,283,317 A | 2/1994 | Saifer | |
| 6,051,251 A | 4/2000 | Zalipsky | |
| 6,355,267 B1 | 3/2002 | Collins | |
| 6,663,885 B1 | 12/2003 | Hager | |
| 6,974,884 B2 | 12/2005 | Raines | |
| 2003/0109690 A1* | 6/2003 | Ruben et al. ................. | 536/23.1 |

FOREIGN PATENT DOCUMENTS

EP    1537858 A1    6/2005
WO   WO 95/34326   12/1995

OTHER PUBLICATIONS

International Search Report from PCT/US2008/001809.
Allen T M et al. (2002) Adventures in Targeting. Journal of Liposome Research, Taylor & Francis, Philadelphia, PA, US, vol. 12, No. 1/02, Jan. 1, 2002, pp. 5-12, XP001126048.
Grant, G. (1992) Synthetic Peptides, A Users Guide, W.H. Freeman and Co. Chapter 3.
Habeeb AF. (1966) Determination of free amino groups in proteins by trinitrobenzenesulfonic acid. Anal Biochem. Mar;14(3):328-36.
Hermanson, G.T. (1996) Bioconjugate Techniques; Academic Press. Chapters 3 and 9.
Lee Tong-Young et al. (2007) Peptide-mediated targeting to tumor blood vessels of lung cancer for drug delivery. Cancer Research, vol. 67, No. 22, Nov. 2007, pp. 10958-10965, XP002488417.
Maeda N et al. (2004) Synthesis of angiogenesis-targeted peptide and hydrophobized polyethylene glycol conjugate. Bioorganic & Medicinal chemistry Letters, Oxford, GB, vol. 14, No. 4, Feb. 23, 2004, pp. 1015-1017, XP002411827.
Moreira J N et al. (2004) Antagonist G-mediated targeting and cytotoxicity of liposomal doxorubicin in CL1-H82 variant small cell lung cancer. Brazilian Journal of Medical and Biological Research, vol. 37, No. 8, Aug. 2004, pp. 1185-1192, XP002488418.
Moreira J N et al. (2001) A growth factor antagonist as a targeting agent for sterically stabilized liposomes in human small cell lung cancer. Biochimica Et Biophysica Acta. Biomembranes, Amsterdam, NL, vol. 1514, No. 2, Oct. 1, 2001, pp. 303-317, XP004319634.
Muggia, F. M. et al. (1997) Phase II study of liposomal doxorubicin in refractory ovarian cancer: antitumor activity and toxicity modification by liposomal encapsulation. J Clin Oncol 15, 987-993.
Pastorino, F. et al. (2006) Targeting liposomal chemotherapy via both tumor cell-specific and tumor vasculature-specific ligands potentiates therapeutic efficacy. Cancer Research, vol. 66, No. 20, Oct. 2006, pp. 10073-10082, XP002488419.
Sugano M et al. (2000) Antibody targeting of doxorubicin-loaded liposomes suppresses the growth and metastatic spread of established human lung tumor xenografts in severe combined immunodeficient mice. Cancer Research, American Association for Cancer Research, Baltimore, MD, vol. 60, No. 24, Dec. 15, 2000, pp. 6942-6949, XP000980029.
Chang De-Kuan, "Identification of a Novel Peptide Specifically Binding to Lung Cancer for Targeted Therapy," Graduate Thesis No. R92444003, indexed and shelved at the National Taiwanese University Library on Sep. 5, 2005.
Partial International Search Report, mailed Apr. 1, 2009, in related International application No. PCT/US2008/084043.
Allen: "Ligand-targeted therapeutics in anticancer therapy" Nature Reviews. Cancer, Natur Publishing Group, London, GB, vol. 2, No. 10, Oct. 1, 2002, pp. 750-763.
Han et al: "Pathogenomic sequence analysis of *Bacillus cereus* and *Bacillus thuringiensis* isolates closely related to *Bacillus anthracia*" Journal of Bacteriology, American Society for Microbiology, US, vol. 188, No. 9, May 1, 2006, pp. 3382-3390.
Du et al: "In vitro panning of a targeting peptide to hepatocarcinoma from a phage display peptide library" Biochemical and Biophysical Research Communications, Academic Press Inc. Orlando, FL, US, vol. 342, No. 3, Apr. 14, 2006, pp. 956-962.

(Continued)

*Primary Examiner* — Michael Burkhart
(74) *Attorney, Agent, or Firm* — Finnegan, Henderson, Farabow, Garrett & Dunner, LLP

(57) ABSTRACT

The invention provides nucleic acids, peptides, and antibodies for use in applications including diagnosis and therapy. The peptides target lung cancer and were identified by phage display. Targeting phage PC5-2 and synthetic peptide SP5-2 were both able to recognize human pulmonary tumor specimens from lung cancer patients. In SCID mice bearing NSCLC xenografts, the targeting phage was able to target tumor masses specifically. When the peptide was coupled to liposomes containing the anti-cancer drugs vinorelbine or doxorubicin, the efficacy of these drugs against human lung cancer xenografts was improved, the survival rate increased, and the drug toxicity was reduced.

13 Claims, 7 Drawing Sheets

OTHER PUBLICATIONS

Krumpe et al: "The Use of Phase-Displayed Peptide Libraries to Develop Tumor-Targeting Drugs" International Journal of Peptide Research and Therapeutics; Formerly Known as Ketters in Peptide Science, Kluwer Academic Publishers, DO, vol. 12, No. 1, Mar. 1, 2006, pp. 79-91.

Halm et al: "A phase II study of pegylated liposomal doxorubicin for treatment of advanced hepatocellular carcinoma." Annals of Oncology: Official Journal of the European Society for Medical Oncology / ESMO Jan. 2000, vol. 11, No. 1, Jan. 2000, pp. 113-114.

Adams, G. P., and Schier, R. (1999). Generating improved single-chain Fv molecules for tumor targeting. Journal of immunological methods 231, 249-260.

Aina, O. H., Marik, J., Liu, R., Lau, D. H., and Lam, K. S. (2005). Identification of novel targeting peptides for human ovarian cancer cells using "one-bead one-compound" combinatorial libraries. Molecular cancer therapeutics 4, 806-813.

Allen, T. M. (2002). Ligand-targeted therapeutics in anticancer therapy. Nature reviews 2, 750-763.

Allen, T. M., and Chonn, A. (1987). Large unilamellar liposomes with low uptake into the reticuloendothelial system. FEBS letters 223, 42-46.

Allen, T. M., and Cullis, P. R. (2004). Drug delivery systems: entering the mainstream. Science 303, 1818-1822.

Allen, T. M., Hansen, C., Martin, F., Redemann, C., and Yau-Young, A. (1991). Liposomes containing synthetic lipid derivatives of poly-(ethylene glycol) show prolonged circulation half-lives in vivo. Biochimica et biophysica acta 1066, 29-36.

Arap, W., Pasqualini, R., and Ruoslahti, E. (1998). Cancer treatment by targeted drug delivery to tumor vasculature in a mouse model. Science 279, 377-380.

Atwell, S., Ultsch, M., De Vos, A. M., and Wells, J. A. (1997). Structural plasticity in a remodeled protein-protein interface. Science 278, 1125-1128.

Barry, M. A., Dower, W. J., and Johnston, S. A. (1996). Toward cell-targeting gene therapy vectors: selection of cell-binding peptides from random peptide-presenting phage libraries. Nat Med 2, 299-305.

Bartel P, Chien CT, Stemglanz R, Fields S. (1993). Elimination of false positives that arise in using the two-hybrid system. Biotechniques 14:920-924.

Blume, G., and Cevc, G. (1990). Liposomes for the sustained drug release in vivo. Biochimica et biophysica acta 1029, 91-97.

Bottger, V., Bottger, A., Howard, S. F., Picksley, S. M., Chene, P., Garcia-Echeverria, C., Hochkeppel, H. K., and Lane, D. P. (1996). Identification of novel mdm2 binding peptides by phage display. Oncogene 13, 2141-2147.

Boyle, P., Gandini, S., and Gray, N. (2000). Epidemiology of lung cancer: a century of great success and ignominious failure. (London: Martin Dunitz).

Castano, A. R., Tangri, S., Miller, J. E., Holcombe, H. R., Jackson, M. R., Huse, W. D., Kronenberg, M., and Peterson, P. A. (1995). Peptide binding and presentation by mouse CD1. Science 269, 223-226.

Chu, Y. W., Yang, P. C., Yang, S. C., Shyu, Y. C., Hendrix, M. J., Wu, R., and Wu, C. W. (1997). Selection of invasive and metastatic subpopulations from a human lung adenocarcinoma cell line. American journal of respiratory cell and molecular biology 17, 353-360.

De Vita F, Orditura M, Infusino S, Martinelli E, Merola MC, Morgillo F, Cosenza A, Di Martino N, Del Genio A, Catalano G. (2001). Preoperative chemo-radiotherapy for carcinoma of the esophagus. Tumori. 87, S24-7.

DeLeo, F. R., Yu, L., Burritt, J. B., Loetterle, L. R., Bond, C. W., Jesaitis, A. J., and Quinn, M. T. (1995). Mapping sites of interaction of p47-phox and flavocytochrome b with random-sequence peptide phage display libraries. Proc Natl Acad Sci U.S.A. 92, 7110-7114.

D'Mello, F., Partidos, C. D., Steward, M. W., and Howard, C. R. (1997). Definition of the primary structure of hepatitis B virus (HBV) pre-S hepatocyte binding domain using random peptide libraries. Virology 237, 319-326.

Drummond, D. C., Meyer, O., Hong, K., Kirpotin, D. B., and Papahadjopoulos, D. (1999). Optimizing liposomes for delivery of chemotherapeutic agents to solid tumors. Pharmacological reviews 51, 691-743.

Dvorak, H. F., Nagy, J. A., and Dvorak, A. M. (1991). Structure of solid tumors and their vasculature: implications for therapy with monoclonal antibodies. Cancer Cells 3, 77-85.

Essler, M., and Ruoslahti, E. (2002). Molecular specialization of breast vasculature: a breast-homing phage-displayed peptide binds to aminopeptidase P in breast vasculature. Proc Natl Acad Sci U.S.A. 99, 2252-2257.

Folgori, A., Tafi, R., Meola, A., Felici, F., Galfre, G., Cortese, R., Monaci, P., and Nicosia, A. (1994). A general strategy to identify mimotopes of pathological antigens using only random peptide libraries and human sera. Embo J 13, 2236-2243.

Fry, W. A., Phillips, J. L., and Menck, H. R. (1999). Ten-year survey of lung cancer treatment and survival in hospitals in the United States: a national cancer data base report. Cancer 86, 1867-1876.

Fu, Y., Shearing, L. N., Haynes, S., Crewther, P., Tilley, L., Anders, R. F., and Foley, M. (1997). Isolation from phage display libraries of single chain variable fragment antibodies that recognize conformational epitopes in the malaria vaccine candidate, apical membrane antigen-1. J Biol Chem 272, 25678-25684.

Gabizon, A., and Papahadjopoulos, D. (1988). Liposome formulations with prolonged circulation time in blood and enhanced uptake by tumors. Proc Natl Acad Sci U.S.A. 85, 6949-6953.

Grant, G. (1992) Synthetic Peptides, A Users Guide, W.H. Freeman and Co.

Gregoriadis, G., Wills, E. J., Swain, C. P., and Tavill, A. S. (1974). Drug-carrier potential of liposomes in cancer chemotherapy. Lancet 1, 1313-1316.

Hall, B. L., Boroughs, J., and Kobrin, B. J. (1998). A novel tumor-specific human single-chain Fv selected from an active specific immunotherapy phage display library. Immunotechnology 4, 127-140.

Hashizume, H., Baluk, P., Morikawa, S., McLean, J. W., Thurston, G., Roberge, S., Jain, R. K., and McDonald, D. M. (2000). Openings between defective endothelial cells explain tumor vessel leakiness. Am J Pathol 156, 1363-1380.

Herbst, R. S., and Sandler, A. B. (2004). Overview of the current status of human epidermal growth factor receptor inhibitors in lung cancer. Clin Lung Cancer 6 Suppl 1, S7-S19.

Hermanson, G.T. (1996) Bioconjugate Techniques; Academic Press.

Hu, W., and Kavanagh, J. J. (2003). Anticancer therapy targeting the apoptotic pathway. Lancet Oncol 4, 721-729.

Huang, S. K., Mayhew, E., Gilani, S., Lasic, D. D., Martin, F. J., and Papahadjopoulos, D. (1992). Pharmacokinetics and therapeutics of sterically stabilized liposomes in mice bearing C-26 colon carcinoma. Cancer research 52, 6774-6781.

Hug, P., and Sleight R.G. (1991). Liposomes for the transformation of eukaryotic cells. Biochim Biophys Acta. 1097, 1-17.

Hunkapiller et al., (1984) A microchemical facility for the analysis and synthesis of genes and proteins Nature, 310, 105-111.

Ihde, D. C. (1992). Chemotherapy of lung cancer. The New England journal of medicine 327, 1434-1441.

Iwabuchi K, Li B, Bartel P, and Fields S. (1993). Use of the two-hybrid system to identify the domain of p53 involved in oligomerization. Oncogene 8:1693-1696.

Jain, R. K. (1996). Delivery of molecular medicine to solid tumors. Science 271, 1079-1080.

Jain, R. K. (1997). The Eugene M. Landis Award Lecture 1996. Delivery of molecular and cellular medicine to solid tumors. Microcirculation 4, 1-23.

Jemal, A., Thomas, A., Murray, T., and Thun, M. (2002). Cancer statistics, 2002. CA: a cancer journal for clinicians 52, 23-47.

Kelly, K., Crowley, J., Bunn, P. A., Jr., Presant, C. A., Grevstad, P. K., Moinpour, C. M., Ramsey, S. D., Wozniak, A. J., Weiss, G. R., Moore, D. F., et al. (2001). Randomized phase III trial of paclitaxel plus carboplatin versus vinorelbine plus cisplatin in the treatment of patients with advanced non-small-cell lung cancer: a Southwest Oncology Group trial. J Clin Oncol 19, 3210-3218.

Klibanov, A. L., Maruyama, K., Torchilin, V. P., and Huang, L. (1990). Amphipathic polyethyleneglycols effectively prolong the circulation time of liposomes. FEBS letters 268, 235-237.

Koivunen, E., Arap, W., Rajotte, D., Landenranta, J., and Pasqualini, R. (1999). Identification of receptor ligands with phage display peptide libraries. J Nucl Med 40, 883-888.

Kraft, S., Diefenbach, B., Mehta, R., Jonczyk, A., Luckenbach, G. A., and Goodman, S. L. (1999). Definition of an unexpected ligand recognition motif for alphav beta6 integrin. J Biol Chem 274, 1979-1985.

Kreitman and Pastan, Immunotoxins in the treatment of hematologic malignancies. Curr Drug Targets. 7, 1301-11 (2006).

Lasic DD, Ceh B, Stuart MC, Guo L, Frederik PM, Barenholz Y. (1995). Transmembrane gradient driven phase transitions within vesicles: lessons for drug delivery. Biochim Biophys Acta. 1239, 145-56.

Lee, T. Y., Wu, H. C., Tseng, Y. L., and Lin, C. T. (2004). A novel peptide specifically binding to nasopharyngeal carcinoma for targeted drug delivery. Cancer Res 64, 8002-8008.

Levy, S. E., and Hyman, S. L. (2005). Novel treatments for autistic spectrum disorders. Mental retardation and developmental disabilities research reviews 11, 131-142.

Li, B., Tom, J. Y., Oare, D., Yen, R., Fairbrother, W. J., Wells, J. A., and Cunningham, B. C. (1995). Minimization of a polypeptide hormone. Science 270, 1657-1660.

Lichtenberg D., and Barenholz, Y. (1988). Methods of Biochemical Analysis, vol. 33, 337-462.

Lin, C. T., Wong, C. I., Chan, W. Y., Tzung, K. W., Ho, J. K., Hsu, M. M., and Chuang, S. M. (1990). Establishment and characterization of two nasopharyngeal carcinoma cell lines. Laboratory investigation; a journal of technical methods and pathology 62, 713-724.

Liu, I. J., Hsueh, P. R., Lin, C. T., Chiu, C. Y., Kao, C. L., Liao, M. Y., and Wu, H. C. (2004). Disease-specific B Cell epitopes for serum antibodies from patients with severe acute respiratory syndrome (SARS) and serologic detection of SARS antibodies by epitope-based peptide antigens. J Infect Dis 190, 797-809.

Lopes de Menezes, D. E. K., M. J.; Gagne, J.-F.; Pilarski,L. M.; Allen, T. M. (1999). Cellular Trafficking and Cytotoxicity of Anti-CD19-Targeted Liposomal Doxorubicin in B Lymphoma Cells. J Liposome Res 9, 199-228.

Lynch, T. J., Adjei, A. A., Bunn, P. A., Jr., DuBois, R. N., Gandara, D. R., Giaccone, G., Govindan, R., Herbst, R. S., Johnson, B. E., Khuri, F. R., et al. (2004). Novel agents in the treatment of lung cancer: conference summary statement. Clin Cancer Res 10, 4199s-4204s.

Madura, K.,Dohmen, R.J., and Varshaysky, A. (1993) N-recognin/Ubc2 interactions in the N-end rule pathway. J. Biol. Chem. 268:12046-12054.

Mantyh, P. W. (2006). Cancer pain and its impact on diagnosis, survival and quality of life. Nat Rev Neurosci 7, 797-809.

Matsumura, Y., and Maeda, H. (1986). A new concept for macromolecular therapeutics in cancer chemotherapy: mechanism of tumoritropic accumulation of proteins and the antitumor agent smancs. Cancer research 46, 6387-6392.

Mazzucchelli, L., Burritt, J. B., Jesaitis, A. J., Nusrat, A., Liang, T. W., Gewirtz, A. T., Schnell, F. J., and Parkos, C. A. (1999). Cell-specific peptide binding by human neutrophils. Blood 93, 1738-1748.

Monfardini, C., et al. (1995) A branched monomethoxypoly(ethylene glycol) for protein modification. Bioconjugate Chem. 6, 62-69.

Neumeister, P., Eibl, M., Zinke-Cerwenka, W., Scarpatetti, M., Sill, H., and Linkesch, W. (2001). Hepatic veno-occlusive disease in two patients with relapsed acute myeloid leukemia treated with anti-CD33 calicheamicin (CMA-676) immunoconjugate. Annals of hematology 80, 119-120.

Ng EW, Shima DT, Calias P, Cunningham ET Jr, Guyer DR, Adamis AP (2006) Pegaptanib, a targeted anti-VEGF aptamer for ocular vascular disease. Nat Rev Drug Discov. 5, 123-32.

Nord, K., Gunneriusson, E., Ringdahl, J., Stahl, S., Uhlen, M., and Nygren, P. A. (1997). Binding proteins selected from combinatorial libraries of an alpha-helical bacterial receptor domain. Nat Biotechnol 15, 772-777.

Northfelt, D. W., Martin, F. J., Working, P., Volberding, P. A., Russell, J., Newman, M., Amantea, M. A., and Kaplan, L. D. (1996). Doxorubicin encapsulated in liposomes containing surface-bound polyethylene glycol: pharmacokinetics, tumor localization, and safety in patients with AIDS-related Kaposi's sarcoma. J Clin Pharmacol 36, 55-63.

Ostoros, G., Kovacs, G., Szondy, K., and Dome, B. (2005). New therapies for non-small cell lung cancer. Orvosi hetilap 146, 1135-1141.

Papahadjopoulos, D., Allen, T. M., Gabizon, A., Mayhew, E., Matthay, K., Huang, S. K., Lee, K. D., Woodle, M. C., Lasic, D. D., Redemann, C., and et al. (1991). Sterically stabilized liposomes: improvements in pharmacokinetics and antitumor therapeutic efficacy. Proc Natl Acad Sci U.S.A. 88, 11460-11464.

Park, J. W., Hong, K., Kirpotin, D. B., Colbern, G., Shalaby, R., Baselga, J., Shao, Y., Nielsen, U. B., Marks, J. D., Moore, D., et al. (2002). Anti-HER2 immunoliposomes: enhanced efficacy attributable to targeted delivery. Clin Cancer Res 8, 1172-1181.

Parkin, D. M., Bray, F. I., and Devesa, S. S. (2001). Cancer burden in the year 2000. The global picture. Eur J Cancer 37 Suppl 8, S4-66.

Pasqualini, R., and Ruoslahti, E. (1996). Organ targeting in vivo using phage display peptide libraries. Nature 380, 364-366.

Pasqualini, R., Koivunen, E., and Ruoslahti, E. (1995). A peptide isolated from phage display libraries is a structural and functional mimic of an RGD-binding site on integrins. J Cell Biol 130, 1189-1196.

Prezzi, C., Nuzzo, M., Meola, A., Delmastro, P., Galfre, G., Cortese, R., Nicosia, A., and Monaci, P. (1996). Selection of antigenic and immunogenic mimics of hepatitis C virus using sera from patients. J Immunol 156, 4504-4513.

Ramalingam, S. (2005). First-line chemotherapy for advanced-stage non-small-cell lung cancer: focus on docetaxel. Clin Lung Cancer 7 Suppl 3, S77-82.

Rosenkilde, M. M., and Schwartz, T. W. (2004). The chemokine system—a major regulator of angiogenesis in health and disease. Apmis 112, 481-495.

Ruoslahti, E. (2002). Specialization of tumour vasculature. Nat Rev Cancer 2, 83-90.

Sapra, P., and Allen, T. M. (2004). Improved outcome when B-cell lymphoma is treated with combinations of immunoliposomal anticancer drugs targeted to both the CD19 and CD20 epitopes. Clin Cancer Res 10, 2530-2537.

Schiller, J. H. (2001). Current standards of care in small-cell and non-small-cell lung cancer. Oncology 61 Suppl 1, 3-13.

Scott, J. K., and Smith, G. P. (1990). Searching for peptide ligands with an epitope library. Science 249, 386-390.

Senior, J. H. (1987). Fate and behavior of liposomes in vivo: a review of controlling factors. Critical reviews in therapeutic drug carrier systems 3, 123-193.

Senior, J., Delgado, C., Fisher, D., Tilcock, C., and Gregoriadis, G. (1991). Influence of surface hydrophilicity of liposomes on their interaction with plasma protein and clearance from the circulation: studies with poly(ethylene glycol)-coated vesicles. Biochimica et biophysica acta 1062, 77-82.

Shockley, T. R., Lin, K., Nagy, J. A., Tompkins, R. G., Dvorak, H. F., and Yarmush, M. L. (1991). Penetration of tumor tissue by antibodies and other immunoproteins. Annals of the New York Academy of Sciences 618, 367-382.

Smith, W. C., McDowell, J. H., Dugger, D. R., Miller, R., Arendt, A., Popp, M. P., and Hargrave, P. A. (1999). Identification of regions of arrestin that bind to rhodopsin. Biochemistry 38, 2752-2761.

Stefano (2006) A conjugate of doxorubicin with lactosaminated albumin enhances the drug concentrations in all the forms of rat hepatocellular carcinomas independently of their differentiation grade. Liver Int. 26, 726-33.

Suter, B., Auerbach, D., and Stagljar, I.(2006). Yeast-based functional genomics and proteomics technologies: the first 15 years and beyond. Biotechniques 40:625-44.

Thomas, G. E., Esteban, J. M., Raubitschek, A., and Wong, J. Y. (1995). gamma-Interferon administration after 90yttrium radiolabeled antibody therapy: survival and hematopoietic toxicity studies. International journal of radiation oncology, biology, physics 31, 529-534.

Thongprasert, S., Sanguanmitra, P., Juthapan, W., and Clinch, J. (1999). Relationship between quality of life and clinical outcomes in advanced non-small cell lung cancer: best supportive care (BSC) versus BSC plus chemotherapy. Lung Cancer 24, 17-24.

Tseng YL, Hong RL, Tao MH, Chang FH. (1999). Sterically stabilized anti-idiotype immunoliposomes improve the therapeutic efficacy of doxorubicin in a murine B-cell lymphoma model. Int J Cancer. 80:723-30.

Weinstein, J. N. (1984). Liposomes as drug carriers in cancer therapy. Cancer treatment reports 68, 127-135.

Wong, C., Weibel, R., Sheets, M., Mach, J. P., and Finnern, R. (2001). Human scFv antibody fragments specific for the epithelial tumour marker MUC-1, selected by phage display on living cells. Cancer Immunol Immunother 50, 93-101.

Woodle, M. C., and Lasic, D. D. (1992). Sterically stabilized liposomes. Biochimica et biophysica acta 1113, 171-199.

Wrighton, N. C., Farrell, F. X., Chang, R., Kashyap, A. K., Barbone, F. P., Mulcahy, L. S., Johnson, D. L., Barrett, R. W., Jolliffe, L. K., and Dower, W. J. (1996). Small peptides as potent mimetics of the protein hormone erythropoietin. Science 273, 458-464.

Wu, H. C., Huang, Y. L., Chao, T. T., Jan, J. T., Huang, J. L., Chiang, H. Y., King, C. C., and Shaio, M. F. (2001). Identification of B-cell epitope of dengue virus type 1 and its application in diagnosis of patients. J Clin Microbiol 39, 977-982.

Wu, H. C., Jung, M. Y., Chiu, C. Y., Chao, T. T., Lai, S. C., Jan, J. T., and Shaio, M. F. (2003). Identification of a dengue virus type 2 (DEN-2) serotype-specific B-cell epitope and detection of DEN-2-immunized animal serum samples using an epitope-based peptide antigen. J Gen Virol 84, 2771-2779.

Wu, N. Z., Da, D., Rudoll, T. L., Needham, D., Whorton, A. R., and Dewhirst, M. W. (1993). Increased microvascular permeability contributes to preferential accumulation of Stealth liposomes in tumor tissue. Cancer research 53, 3765-3770.

Yuan, F., Leunig, M., Huang, S. K., Berk, D. A., Papahadjopoulos, D., and Jain, R. K. (1994). Microvascular permeability and interstitial penetration of sterically stabilized (stealth) liposomes in a human tumor xenograft. Cancer Res 54, 3352-3356.

Zalipsky, S. (1995) Functionalized poly(ethylene glycol) for preparation of biologically relevant conjugates. Bioconjugate Chem., 6:150-165.

Zalipsky, S., Mullah, N., Harding, J. A., Gittelman, J., Guo, L., and DeFrees, S. A. (1997). Poly(ethylene glycol)-grafted liposomes with oligopeptide or oligosaccharide ligands appended to the termini of the polymer chains. Bioconjugate chemistry 8, 111-118.

Zervos A.S., Gyuris, J., and Brent, R. (1993). Mxi1, a protein that specifically interacts with Max to bind Myc-Max recognition sites. Cell. 72(2):223-32.

* cited by examiner

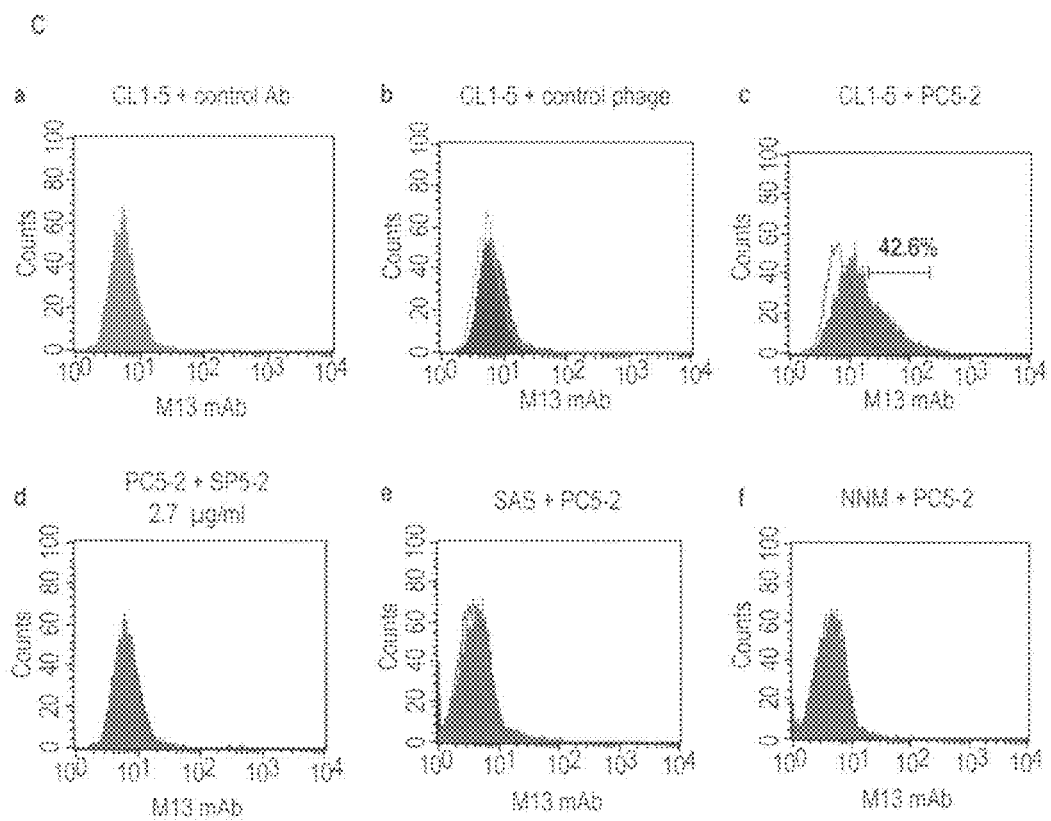
Fig. 2, continued

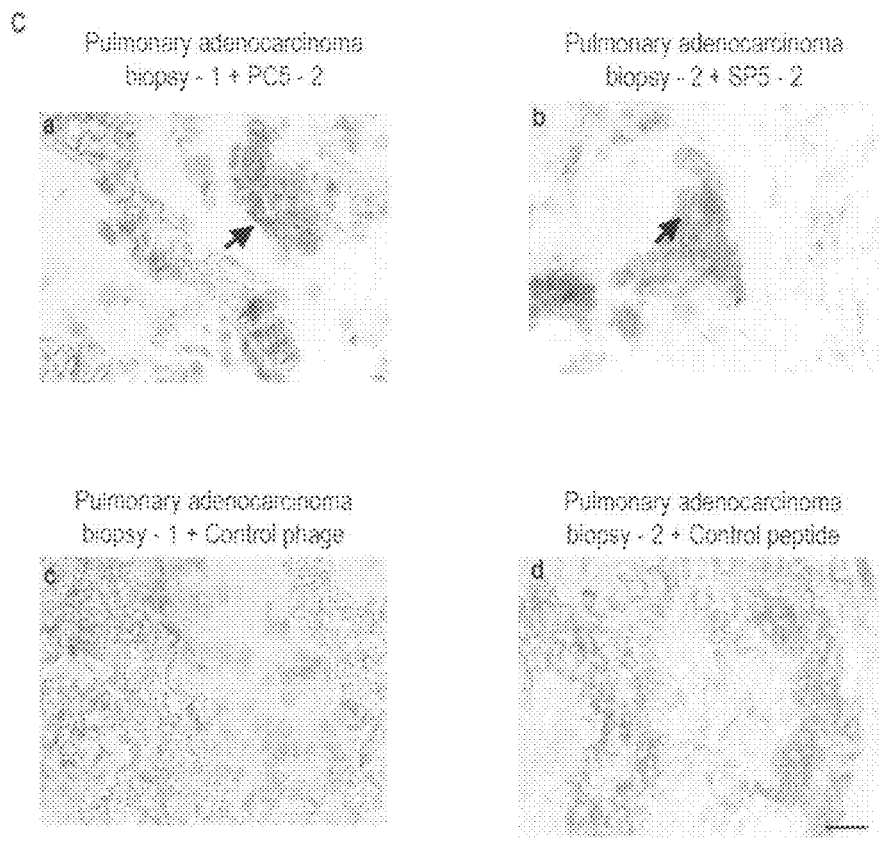
Fig. 3, continued

LUNG CANCER-TARGETED PEPTIDES AND APPLICATIONS THEREOF

PRIORITY CLAIM

This application claims priority to provisional applications 60/900,973, filed Feb. 13, 2007, and 60/901,085, filed Feb. 14, 2007, which are incorporated by reference in their entirety.

BACKGROUND OF THE INVENTION

Lung cancer is the leading cause of cancer-related mortality in the world. The five-year survival rate is less than 15% for patients with advanced non-small cell lung cancer (NSCLC). Lack of tumor specificity remains a major problem for chemotherapies in which side effects prevent the delivery of drug dosages needed to eliminate the majority of cancer cells. Ligand-mediated target therapy might, however, render chemotherapy more tumor specific and less toxic, and may useful for the development of novel therapies for cancer.

Even though the pharmaceutical industry has been successful in discovering many new cytotoxic drugs that are potential candidates for the treatment of cancer, this life-threatening disease still causes more than 7 million deaths every year worldwide and the number is growing (Mantyh, 2006). The clinical use of most conventional chemotherapeutics is often limited by inadequate delivery of therapeutic drug concentrations to the tumor target tissue or by severe and harmful toxic effects on normal organs. It is therefore of importance to develop novel microcarrier technologies that can be used for targeted drug delivery to tumors and thereby improve the therapeutic index of the carried drugs.

Phage display, a selection technique in which a peptide or protein is expressed as a fusion with a coat protein of bacteriophage, results in display of the fusion peptide or protein on the surface of the virion. Phage-displayed random peptide libraries provide opportunities to map B-cell epitopes (D'Mello et al., 1997; Fu et al., 1997; Scott and Smith, 1990; Wu et al., 2001; Wu et al., 2003) and protein-protein contacts (Atwell et al., 1997; Bottger et al., 1996; Nord et al., 1997; Smith et al., 1999), select bioactive peptides bound to receptors (Koivunen et al., 1999; Li et al., 1995; Wrighton et al., 1996) or proteins (Bottger et al., 1996; Castano et al., 1995; DeLeo et al., 1995; Kraft et al., 1999; Pasqualini et al., 1995), search for disease-specific antigen mimics (Folgori et al., 1994; Liu et al., 2004; Prezzi et al., 1996), and determine cell- (Barry et al., 1996; Lee et al., 2004; Mazzucchelli et al., 1999) and organ-specific peptides (Arap et al., 1998; Essler and Ruoslahti, 2002; Pasqualini et al., 1995; Pasqualini and Ruoslahti, 1996).

Liposomes were suggested as drug carriers in cancer chemotherapy (Gregoriadis et al., 1974). Since then, the interest in liposomes has increased and liposome systems are now being extensively studied as drug carriers. Three basic requirements are desired for liposomes to be used in delivering drugs specifically to cancerous tissue: (i) prolonged blood circulation, (ii) sufficient tumor accumulation, (iii) controlled drug release and uptake by tumor cells with a release profile matching the pharmacodynamics of the drug.

Initially, the research in liposome drug delivery systems suffered from very fast blood clearance by the reticuloendothelial system (RES). It was recognized that particle size, surface charge (Weinstein, 1984), and liposome composition had a strong influence on the clearance profile (e.g., incorporation of phosphatidylinositols or monosialogangliosides prolongs liposome circulation in the blood) (Allen and Chonn, 1987; Gabizon and Papahadjopoulos, 1988; Senior, 1987). This uptake may be evaded by 'stealth' liposomes, which preferentially exit the circulation via leaky capillaries and are predicted to accumulate in tumors exhibiting extensive neo-vascularization leading to higher concentrations and enhanced antitumor activity (Wu et al., 1993). However, liposomes were only fully recognized as successful drug delivery candidates when it was discovered that liposomes coated with the synthetic polymer polyethyleneglycol (PEG) had significantly increased half-life in the blood (Allen et al., 1991; Blume and Cevc, 1990; Klibanov et al., 1990; Papahadjopoulos et al., 1991; Senior et al., 1991). The pegylated liposomes are long circulating due to a highly hydrated and protected liposome surface, which inhibits protein adsorption and opsonization of the liposomes (Woodle and Lasic, 1992). Having solved the problems of fast opsonization and clearance, providing liposomes with up to 72 h half-life in the blood (Drummond et al., 1999), the next challenge was to get the liposomes to accumulate in the tumor tissue through active targeting. The use of targeting liposomes may potentially lead to significantly enhanced drug release at the tumor target site and increased therapeutic efficacy (Lee et al., 2004; Park et al., 2002).

The drug delivery research field has successfully constructed long circulating liposomes that accumulate in tumor tissue where the entrapped drugs then have to leak out of the liposomes by passive diffusion, unless there is an active trigger present. The use of site-specific triggers that can release drugs specifically in diseased tissue is one way of increasing drug bioavailability at the tumor target site. Another way of optimizing drug bioavailability is to obtain a higher degree of liposome accumulation by active targeting. Furthermore, the combination of active targeting with active triggering may potentially lead to significantly enhanced and specific drug release at the tumor target site (Lee et al., 2004; Park et al., 2002).

One major limitation of using monoclonal antibodies to target cancer is that the antibody molecule is relatively large with a molecular weight (MW) of 150,000. This molecule has difficulty reaching the interior of large tumor masses where the blood supply is inadequate (Dvorak et al., 1991; Jain, 1997; Shockley et al., 1991). To overcome this problem, some researchers are now developing antitumor single chain Fv (scFv) antibodies that are smaller in size, MW 25,000 (Adams and Schier, 1999; Hall et al., 1998; Wong et al., 2001). Another major problem with monoclonal antibody therapy is the nonspecific uptake of the antibody molecules into the reticuloendothelial system such as the liver, spleen, and bone marrow. The dose-limiting toxicities of radiolabeled or toxin conjugated antibody are liver and bone marrow toxicities (Neumeister et al., 2001; Thomas et al., 1995). In contrast, peptides can be considerably smaller than monoclonal antibodies and they generally do not bind to the reticuloendothelial system (Aina et al., 2005). They are chemically stable and relatively easy to manufacture. In addition, the effective tissue penetration of short synthetic peptides, in combination with their selective binding and internalizing capacity by cancer cells, make these agents ideal candidates for delivery of therapeutics such as cytotoxic drugs, oligonucleotides, toxins, and radioactive molecules. In contrast to viral delivery vectors and monoclonal antibodies, peptides are nearly invisible to the immune system and are expected to cause minimal or no side effects (Levy and Hyman, 2005). Therefore, identification of targeting ligands and development of ligand-targeted liposomes is highly desirable.

We believe that promising novel therapy for NSCLC will require tumor targeted approaches that will allow greater tumor specificity and less toxicity. Here, we describe the isolation and identification of peptides, including SP5-2 which could bind specifically to several NSCLC cell lines and human biopsy specimens from lung cancer patients. When coupled to liposomes containing vinorelbine or doxorubicin, the targeting peptide SP5-2 enhanced the therapeutic index of the drugs against human lung cancer xenografts in SCID mice. Our results indicate that this targeting peptide, and the other peptides identified in our study, have strong clinical potential as a drug delivery agents in the treatment of lung cancer.

Screening phage display libraries against specific target tissues would therefore be a direct and fast method in identifying peptide sequences, which are used for targeting of drugs, gene delivery vectors or other therapeutic agents.

SUMMARY OF THE INVENTION

The present invention, inter alia, comprises the following, alone or in combination:

The invention provides polynucleotides, and variants thereof, including SEQ ID NO: 1, SEQ ID NO: 3, SEQ ID NO: 5, SEQ ID NO: 7, SEQ ID NO: 9, SEQ ID NO: 1, SEQ ID NO: 13, SEQ ID NO: 15, SEQ ID NO: 17, and SEQ ID NO: 19.

The invention provides peptides, and variants thereof, including SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, and SEQ ID NO: 20. In one embodiment, the peptide comprises SEQ ID NO: 2, or a variant thereof. In another embodiment, the peptide comprises SEQ ID NO: 2. In another embodiment, the peptides comprise fusion proteins. In another embodiment, the peptides comprise one or more labels. The labels may include FITC, biotin, and a radioisotope. In another embodiment, the peptides are conjugated to one or more drugs. The drugs may include doxorubicin, vinorelbine, an oligonucleotide, a toxin, an anti-VEGF aptamer, and a radioactive molecule.

The invention provides antibodies that bind to the peptides of the invention, or variants thereof, including SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, and SEQ ID NO: 20.

The invention provides liposomes comprising one or more of the peptides of the invention, including a peptide comprising SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, and SEQ ID NO: 20. In one embodiment, the liposomes comprise a peptide comprising SEQ ID NO: 2, or a variant thereof. In another embodiment, the liposome comprises a peptide comprising SEQ ID NO: 2. The liposomes may comprise one or more drugs. The drugs may include doxorubicin, vinorelbine, an oligonucleotide, a toxin, an anti-VEGF aptamer, and a radioactive molecule. In one embodiment the drug is doxorubicin. In another embodiment, the drug is vinorelbine. The doxorubicin can be in an amount from about 110 µg to about 130 µg per µmol phospholipid. In an embodiment, the liposomes have diameters from about 65 nm to about 75 nm. In another embodiment, the number of peptide molecules per liposome is from about 300 to about 500. The liposomes may comprise a pharmaceutically acceptable carrier.

The invention provides methods of treating cancer comprising contacting a subject with a liposome comprising one or more a chemotherapeutic drugs, and a peptide, or variant thereof selected from the group consisting of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, and SEQ ID NO: 20. The chemotherapeteutic drug may be selected from the group consisting of doxorubicin, vinorelbine, an oligonucleotide, a toxin, and a radioactive molecule. In one embodiment, the chemotherapeutic drug is doxorubicin. In another embodiment, the chemotherapeutic drug is vinorelbine. In one embodiment, the cancer is a lung cancer selected from the group consisting of NSCLC, and SCLC.

The invention provides methods for detecting cancer cells in a specimen comprising contacting a specimen with the peptide of claim 2 under conditions that allow binding of the peptide to the cancer cells of said specimen, and detecting the binding of said polypeptide to said cancer cells of said specimen using the antibody of claim 8. In one embodiment, the peptide is a fusion protein comprising an epitope, and the fusion protein is detected using an antibody to the epitope of the fusion protein. In another embodiment, the peptide is labeled, and the peptide is detected by detecting the label. In one embodiment, the label comprises FITC. In another embodiment, the label comprises biotin.

The invention provides a method of identifying a biological molecule, that binds to the peptide of the invention comprising contacting a cellular extract with the peptide of the invention under conditions that allow formation of a complex comprising the peptide and the target protein, and analyzing the complex to identify the target protein.

The invention provides a polynucleotide that hybridizes to the complement of polynucleotide or variant thereof of claim 1 under stringent conditions.

The invention provides a vector comprising the polynucleotide of claim 1.

The invention provides a host cell comprising a vector comprising the polynucleotide of claim 1.

The invention provides a polypeptide encoded by a polynucleotide that hybridizes to the complement of polynucleotide or variant thereof of claim 1 under stringent conditions.

BRIEF DESCRIPTION OF THE FIGURES AND TABLE

Figure 1:
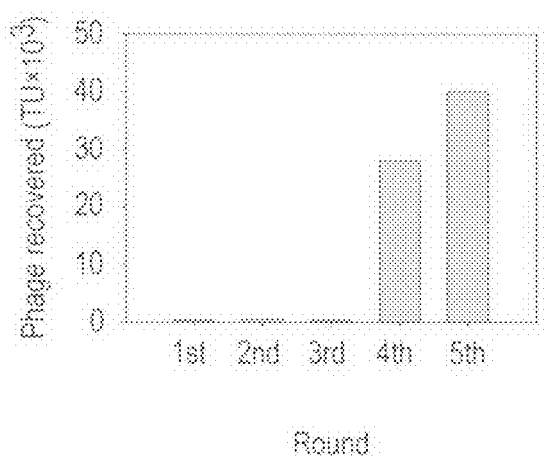
FIG. 1. Isolation of NSCLC cell-specific phage using in vitro phage display.

(A) Change in tumor size of mice treated with SP5-2-Lipo-Vin. (B) Change in body weight of treated mice. (C) Survival curve of mice treated with SP5-2-Lipo-Vin. (D) Change in tumor size of mice treated with SP5-2-Lipo-Dox.

BRIEF DESCRIPTION OF THE TABLE

Table 1 provides phage-displayed peptide sequences from phage selected from NSCLC xenografts.

DETAILED DESCRIPTION OF THE INVENTION

Lung cancer is one of the most common malignant tumors in developed countries, and is an increasing problem in developing countries (Boyle et al., 2000). There are two major types of lung cancer: small cell lung cancer (SCLC) and non-small cell lung cancer (NSCLC). NSCLC makes up about 80 percent of the cases, and SCLC approximately 20 percent (Schiller, 2001). According to the American Cancer Society, the five-year survival rate is less than 15% for patients with NSCLC. NSCLC has proven to be particularly difficult to treat (Fry et al., 1999; Ihde, 1992). Malignant tumors of the lung cause over one million deaths worldwide, and have become an epidemic disease (Jemal et al., 2002). Lung cancer is a deadly illness because of poor diagnosis and the lack of efficacious therapy. Surgery is the recommended treatment while chemotherapy and radiotherapy have a role either as a part of a treatment strategy to cure locally advanced disease or as a palliative therapy for metastatic tumors (Thongprasert et al., 1999). However, the lack of cytotoxic drug specificity and the consequent generation of toxic side effects, particularly when high doses are administered, often limits the use of this treatment modality. Thus, there is a great need to understand the molecular alterations that confer a poor prognosis and to use this information to improve diagnosis and patient management, and a need in the art for more effective cancer treatments.

The main goal of cancer therapy is to eradicate cancer cells completely, while sparing normal tissues. This goal requires the selective targeting of cancer cells at the site of malignancy. The selective toxicity of an anticancer drug can be increased by either increasing the dose of the drug that reaches the diseased tissue or by decreasing the dose that reaches normal tissues, but ideally both will occur. Therefore, ligand-mediated targeting of anticancer therapeutics is being explored (Allen, 2002).

The basic principle that underlies ligand-targeted therapy is the delivery of chemotherapeutic drugs to cancer cells or cancer-associated endothelia, fibroblasts and lymphocytes. Selective targeting of cancer cells and their microenvironment can be enhanced by associating the drugs with molecules that bind to antigens or receptors or other molecules that are either uniquely expressed or overexpressed on the target cells relative to normal tissues (Allen and Cullis, 2004; Arap et al., 1998; Hu and Kavanagh, 2003; Rosenkilde and Schwartz, 2004). This strategy allows specific delivery of drugs to the cancer cells and increases the therapeutic efficacy for anticancer treatment (Allen and Cullis, 2004; Arap et al., 1998; Hu and Kavanagh, 2003; Rosenkilde and Schwartz, 2004).

Cytotoxic drugs, such as cyclophosphamide, doxorubicin, cisplatin, paclitaxel, vinorelbine, and several dozen others, have been useful in treating many types of cancer because their lethal activity is highest in cells that are undergoing continual proliferation, and the cells of many common tumor types are actively dividing. Normal tissues that are typically the most vulnerable to the effects of cytotoxicity include those that are frequently dividing such as bone marrow, the epithelial lining of the gastrointestinal tract, and hair follicles (Herbst and Sandler, 2004). It is well-known that chemotherapy can prolong the survival of patients with NSCLC. The recently published clinical trials of chemotherapy for advanced NSCLC used drugs developed in the 1990s such as paclitaxel, docetaxel, gemcitabine, vinorelbine, and irinotecan (Lynch et al., 2004). Accordingly, the current standard chemotherapy for elderly patients with advanced NSCLC is the use of vinorelbine for single-agent chemotherapy (Kelly et al., 2001). Vinorelbine is a vinca alkaloid that interferes with microtubule assembly. The antitumor activity of vinorelbine is thought to be due primarily to inhibition of mitosis at metaphase through its interaction with tubulin (Ramalingam, 2005). Although cytotoxic chemotherapy has had a major impact on the treatment of some cancers, its efficacy against most solid tumors is limited (Parkin et al., 2001).

We used the phage display technique to identify phage clones that could specifically bind to NSCLC cell lines. The peptides are also described in terms to their ability to home to or target cancer cells. The terms "home," "homing," "target," and "targeting" are used interchangeably. At the fifth round of biopanning, the selected phage clones had 40-fold increased binding activity compared with the first round of biopanning. After screening the specific binding phages on CL1-5 cells by ELISA, the results revealed that one phage clone called PC5-2 was the most abundant phage (made up 90% of selected phages) binding to CL1-5 cells (Table 1).

Figure 2:
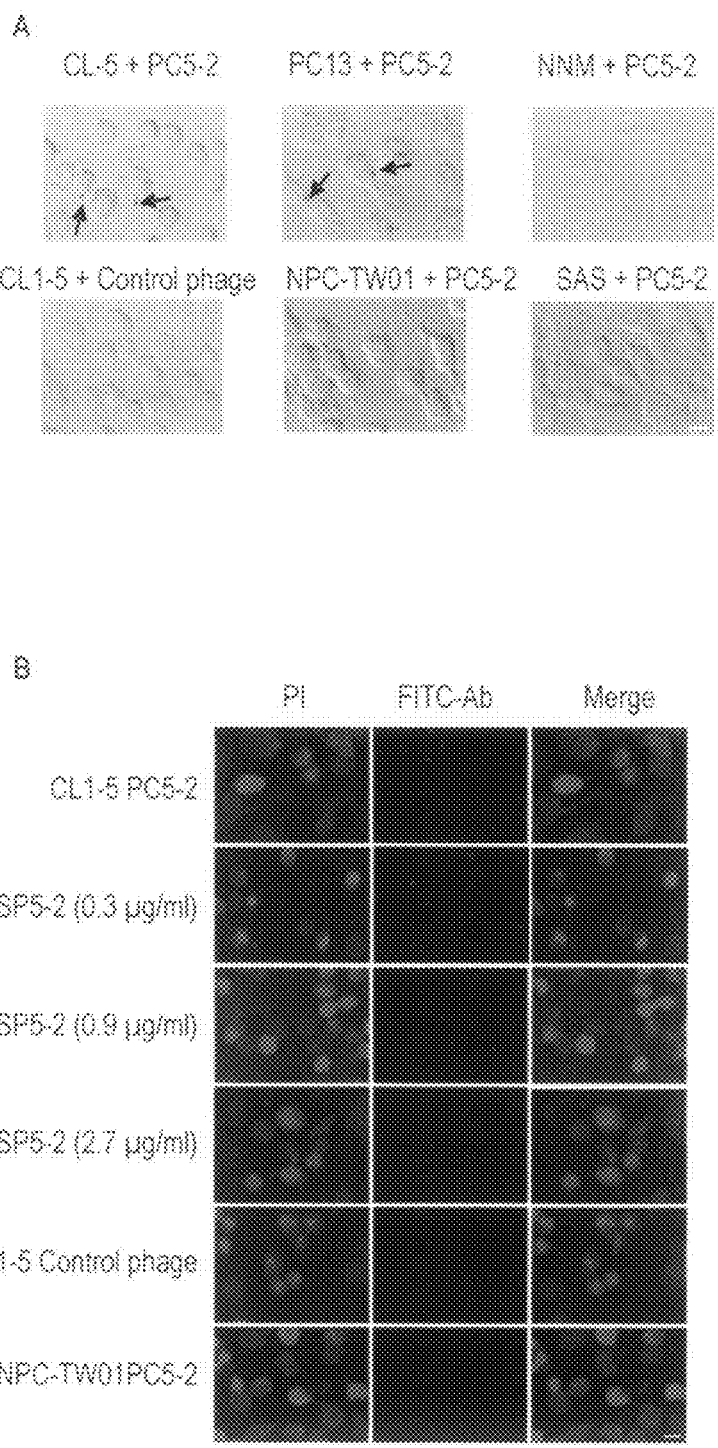
FIG. 2. Identification of specific phage clones binding to NSCLC cells. (A) Visualization of binding of PC5-2 in CL1-5 and PC13 lung cancer cells. Scale bar: 10 µm. (B) PC5-2 exhibits binding to CL1-5 cells and is inhibited by SP5-2 synthetic peptide. Scale bar: 10 µm. (C) Binding profiles of PC5-2 to cell surface of CL1-5 cells measured by flow cytometry.

Immunohistochemical study further confirmed that PC5-2 has specific binding activity to NSCLC cells (FIG. 2A). To verify the PC5-2 displayed peptide could specifically bind to NSCLC cells, we used its cognate synthetic peptide, SP5-2, to compete the same binding site of the PC5-2 on the cells. Results from fluorescent staining and flow cytometry analysis showed that SP5-2 could inhibit the binding of PC5-2 to NSCLC cells (FIG. 2B and FIG. 2C). These results indicate that PC5-2 interacted with cancer cells by its displayed peptide and not by another part of the phage particle.

Figure 3:
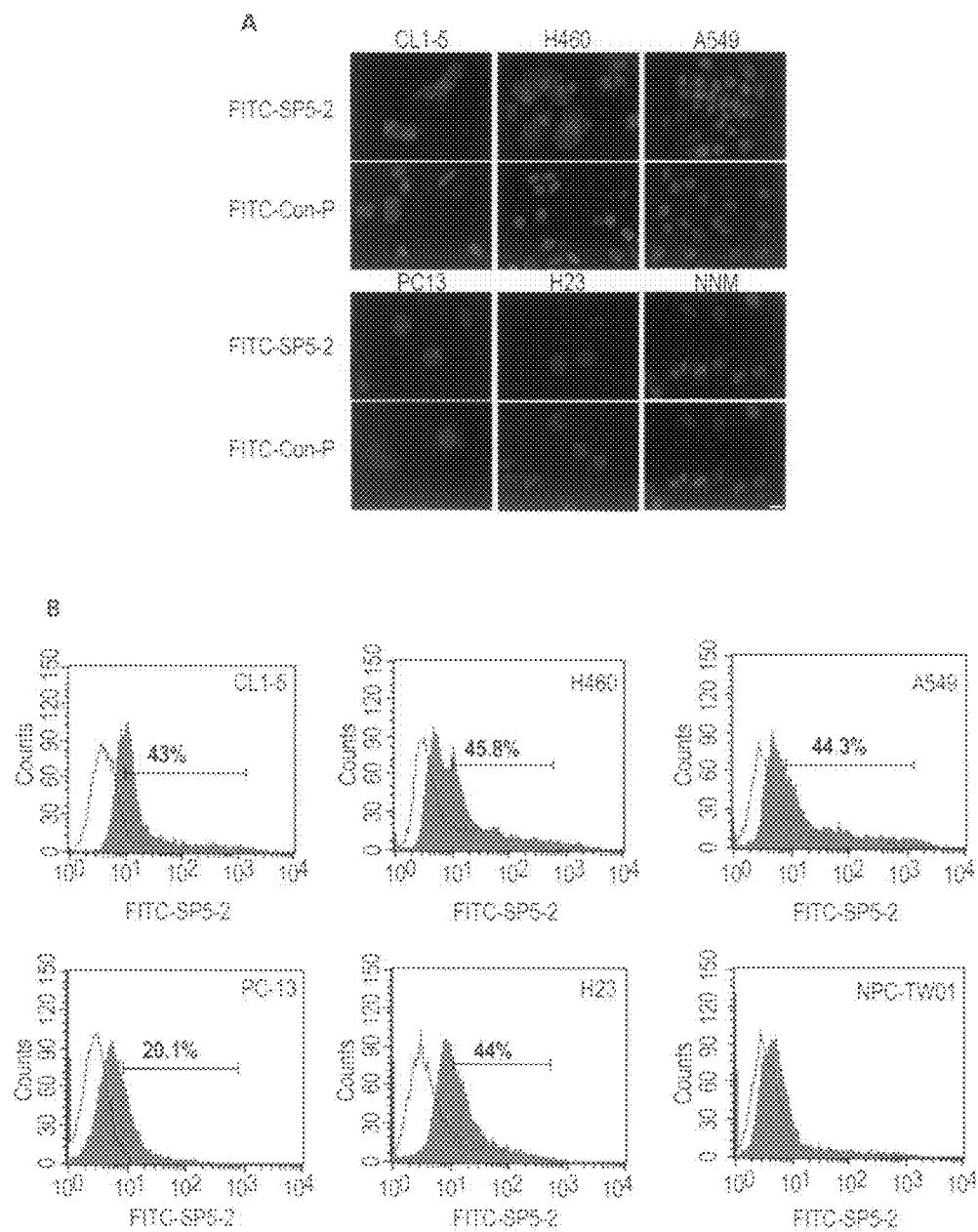
FIG. 3. The binding activity of targeting peptide with NSCLC cells and human lung cancer biopsy specimens. (A) FITC-labeled SP5-2 binds to five NSCLC cell lines but not to normal epithelial cells (NNM). Scale bar: 10 µm. (B) FITC-labeled SP5-2 binds NSCLC cell lines (C) PC5-2 and SP5-2 bind to pulmonary adenocarcinoma biopsy specimens from lung cancer patients. Scale bar: 25 µm.

To verify how many NSCLC cell lines expressed the target molecule that could be recognized by SP5-2, we synthesized FITC-labeled SP5-2 to characterize its binding activity. Using immunofluorescent staining and flow cytometry to analyze five different types of NSCLC cell lines, we determined that the cell lines showed differing degrees of cell surface binding by SP5-2 (FIGS. 3A and B). It is clear that the plasma membranes of these five NSCLC cell lines express an unknown molecule that can be recognized by SP5-2. When we measured the binding ratio of SP5-2 with NSCLC cell lines, 20.1% to 45.8% of NSCLC cells in each line could be detected by SP5-2 (FIG. 3B).

To verify whether SP5-2 has a potential as a drug delivery agent for diagnosis and treatment of NSCLC, we synthesized a biotin-labeled PC5-2 and used it to detect pulmonary adenocarcinoma biopsy specimens from lung cancer patients by immunohistochemistry. Both PC5-2 and biotin-labeled SP5-2 could detect the NSCLC biopsy specimens (FIG. 3C). Fifty percent (5/10) of pulmonary adenocarcinoma from 10 patients express the target molecule that could be detected by the peptide.

Figure 4:
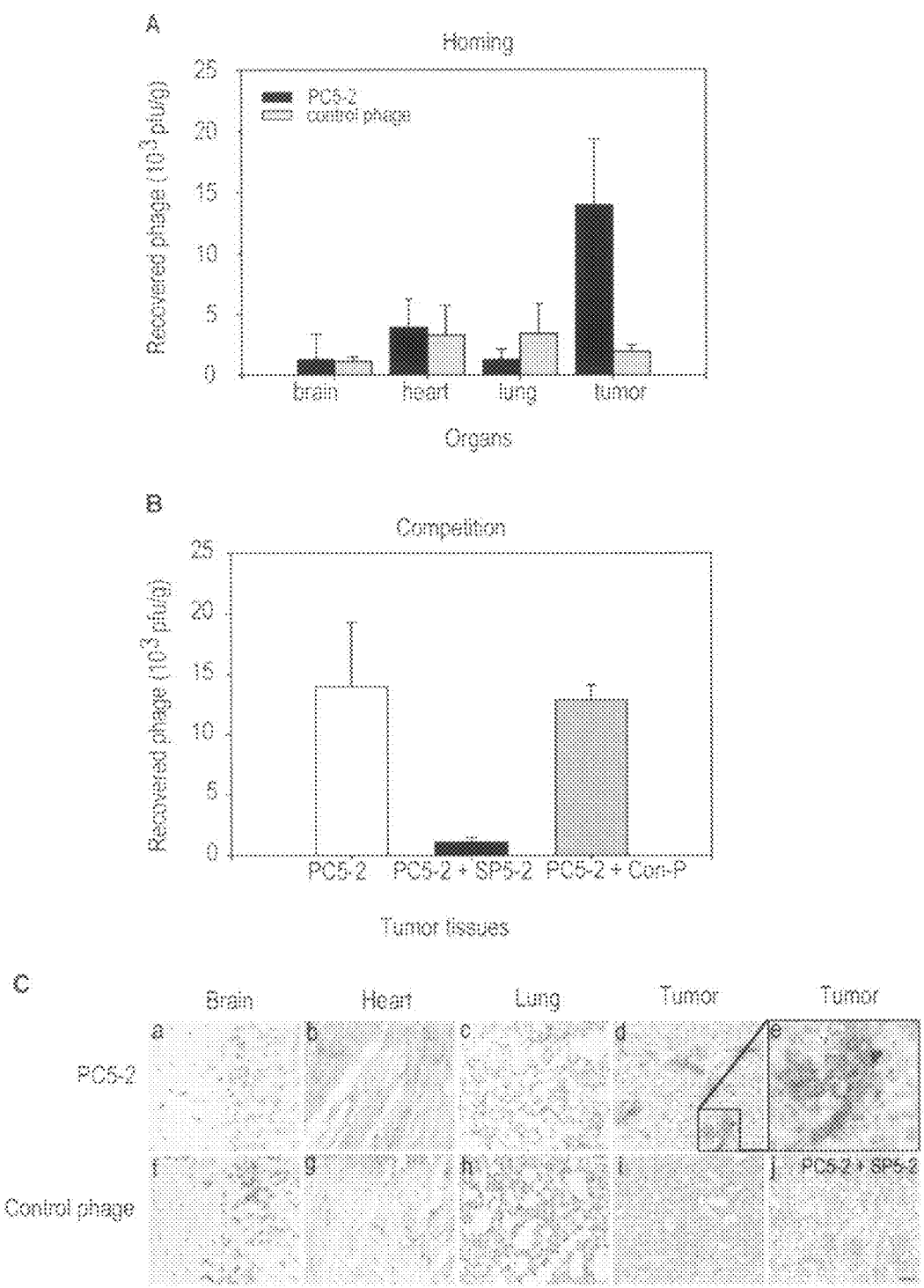
FIG. 4. Verification of tumor-homing ability of PC5-2 in vivo. (A) Recovery of PC5-2 in tumors relative to brain, lung and heart. (B) Targeting of PC5-2 to tumor tissues is competitively inhibited by SP5-2, but not by control peptides. (C) localization of PC5-2 in CL1-5-derived xenografts. Scale bar: 25 µm FIG. 5. Treatment of SCID mice bearing human lung cancer xenografts with SP5-2-Lipo-Vin and SP5-2-Lipo-Dox.

To test the tumor homing ability of PC5-2, we used mice bearing a human lung cancer xenograft as a model. An in vivo homing experiment showed that PC5-2 has a higher affinity for tumor tissue, and the phage was not found to bind specifically to normal organs, such as lung, heart and brain (FIG. 4A). When a peptide competitive inhibition assay was performed, the binding activity of PC5-2 with tumor tissues was inhibited by synthetic peptide SP5-2 (FIG. 4B). These results suggest that the synthetic peptide could specifically bind to the same binding sites as the respective phage.

To identify the localization of homing phages in tumor masses and normal organs, PC5-2 was i.v. injected into lung cancer bearing SCID mice and tissue sections were then used to localize the phages with anti-M13 monoclonal antibodies. The immunohistochemical localization of PC5-2 demonstrated that the phages were localized in tumor tissues, but not in brain, lung, and heart tissues (FIG. 4C), further supporting our conclusion that PC5-2 can specifically bind to xenograft tumor cells but not normal tissues and cells. Our results indicate that PC5-2, and the other peptides that were isolated through biopanning, can be used as drug delivery agents for ligand-targeted therapy or as diagnostic reagents for lung cancer or other cancers.

To develop ligand-targeted therapy, we prepared SP5-2-linked liposomes that carried chemotherapeutic drugs vinorelbine (SP5-2-Lipo-Vin) or doxorubicin (SP5-2-Lipo-Dox). SP5-2-Lipo-Vin showed an improvement of therapeutic efficacy in SCID mice bearing NSCLC xenografts with no specific side effects to the animals (FIGS. 5A and B) and no histological evidence of organotoxicity. Comparing the effect of SP5-2-Lipo-Vin and Lipo-Vin on tumor growth, we found a marked difference in tumor size at day 42 after therapy ($P<0.05$), though the tumor growth was also partially inhibited by Lipo-Vin treatment (FIG. 5A). This partial inhibition by Lipo-Vin may be due to the accumulation of non-specific attachment of liposomes in tumor tissue through a "leaky" microvasculature and impaired lymphatic system supporting the tumor area (Huang et al., 1992; Jain, 1996; Matsumura and Maeda, 1986). This effect is often referred to as the enhanced permeability and retention effect (Matsumura and Maeda, 1986). Passively targeted liposome Lipo-Vin can be used to treat cancer, but it can be improved by the higher and more selective anticancer activity made possible by ligand-targeted therapy, sometimes termed 'active' targeting. In addition, to enhancing the antitumor efficacy, SP5-2-Lipo-Vin also decreased the side effects compared with Lipo-Vin (FIG. 5B).

Figure 5:
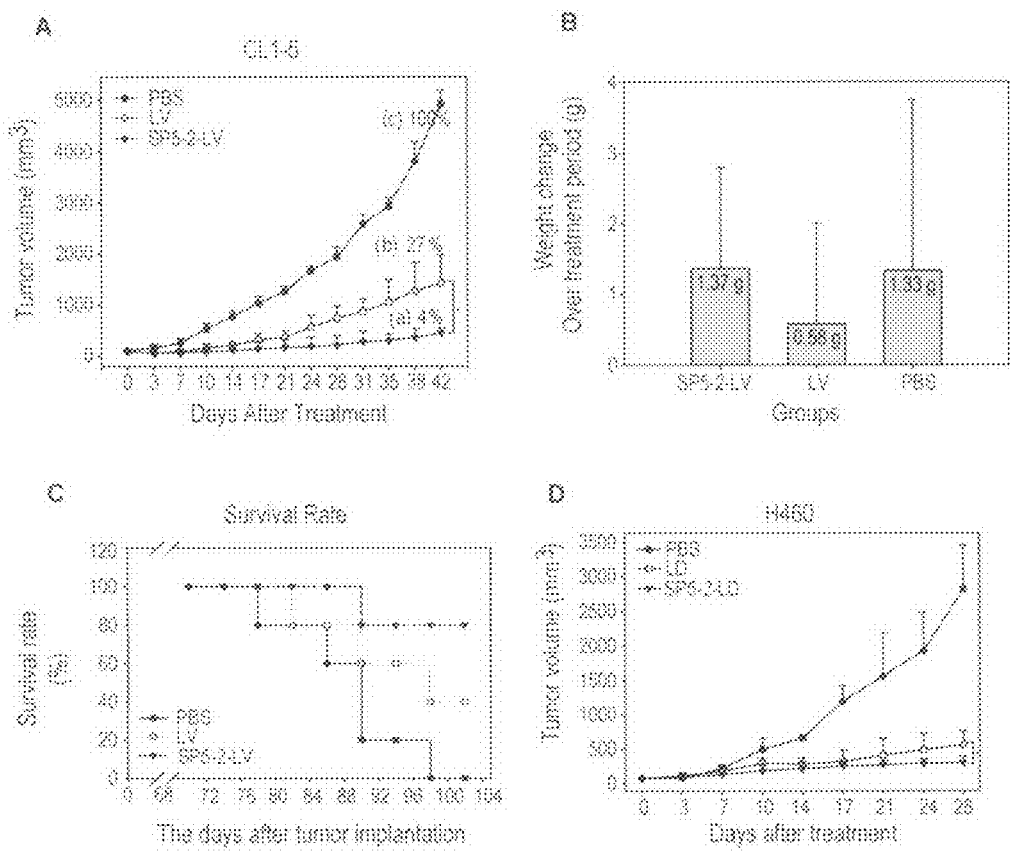

We compared the animal survival rate after treatment with SP5-2-Lipo-Vin, Lipo-Vin and PBS solution separately and observed the animals for 102 days. The SP5-2-Lipo-Vin treated group had a 80% survival rate, while the Lipo-Vin treated group had only a 40% survival rate, and the PBS treated group showed no survival of tumor bearing mice (0% survival rate) (FIG. 5C). These phenomena suggest that conjugation of Lipo-Vin with the SP5-2 peptide provides more efficacy in inhibiting tumor growth and markedly prolongs the life of the SCID mice bearing NSCLC xenografts. The SP5-2 peptide not only enhanced the efficacy of the drug aganist NSCLC xenografts in SCID mice but also reduced its toxicity. The body weight change of Lipo-Vin treated mice decreased 60% relative to the SP5-2-Lipo-Vin and PBS treated mice (FIG. 5B). The enhanced therapeutic index with SP5-2-Lipo-Vin demonstrates a significant clinical potential of the targeted drug delivery system for NSCLC (FIG. 5).

These results indicate that our tumor-specific homing peptide can not only function as a therapeutic agent for targeting therapy, but can also serve as a molecular tool for targeting tumor tissue of NSCLC as an imaging probe. This target ligand may also useful to identify the target protein or other molecule on plasma membrane of NSCLC.

In summary, using phage-displayed peptide libraries to screen NSCLC cells we have identified novel peptides, including SP5-2, which can specifically bind to cell surface of NSCLC cells both in vitro and in vivo. The targeting peptides can be linked to liposomes containing vinorelbine, doxorubicin, or other agents, resulting in increased therapeutic efficacy and survival rate without systemic side effects. The SP5-2 peptide appears to be an excellent agent for drug delivery to NSCLC cells, and has strong clinical potential as a drug delivery system in the treatment of NSCLC.

REFERENCES

Adams, G. P., and Schier, R. (1999). Generating improved single-chain Fv molecules for tumor targeting. Journal of immunological methods 231, 249-260.

Aina, O. H., Marik, J., Liu, R., Lau, D. H., and Lam, K. S. (2005). Identification of novel targeting peptides for human ovarian cancer cells using "one-bead one-compound" combinatorial libraries. Molecular cancer therapeutics 4, 806-813.

Allen, T. M. (2002). Ligand-targeted therapeutics in anticancer therapy. Nature reviews 2, 750-763.

Allen, T. M., and Chonn, A. (1987). Large unilamellar liposomes with low uptake into the reticuloendothelial system. FEBS letters 223, 42-46.

Allen, T. M., and Cullis, P. R. (2004). Drug delivery systems: entering the mainstream. Science 303, 1818-1822.

Allen, T. M., Hansen, C., Martin, F., Redemann, C., and Yau-Young, A. (1991). Liposomes containing synthetic lipid derivatives of poly(ethylene glycol) show prolonged circulation half-lives in vivo. Biochimica et biophysica acta 1066, 29-36.

Arap, W., Pasqualini, R., and Ruoslahti, E. (1998). Cancer treatment by targeted drug delivery to tumor vasculature in a mouse model. Science 279, 377-380.

Atwell, S., Ultsch, M., De Vos, A. M., and Wells, J. A. (1997). Structural plasticity in a remodeled protein-protein interface. Science 278, 1125-1128.

Barry, M. A., Dower, W. J., and Johnston, S. A. (1996). Toward cell-targeting gene therapy vectors: selection of cell-binding peptides from random peptide-presenting phage libraries. Nat Med 2, 299-305.

Blume, G., and Cevc, G. (1990). Liposomes for the sustained drug release in vivo. Biochimica et biophysica acta 1029, 91-97.

Bottger, V., Bottger, A., Howard, S. F., Picksley, S. M., Chene, P., Garcia-Echeverria, C., Hochkeppel, H. K., and Lane, D. P. (1996). Identification of novel mdm2 binding peptides by phage display. Oncogene 13, 2141-2147.

Boyle, P., Gandini, S., and Gray, N. (2000). Epidemiology of lung cancer: a century of great success and ignominious failure., (London: Martin Dunitz).

Castano, A. R., Tangri, S., Miller, J. E., Holcombe, H. R., Jackson, M. R., Huse, W. D., Kronenberg, M., and Peterson, P. A. (1995). Peptide binding and presentation by mouse CD1. Science 269, 223-226.

Chu, Y. W., Yang, P. C., Yang, S. C., Shyu, Y. C., Hendrix, M. J., Wu, R., and Wu, C. W. (1997). Selection of invasive and metastatic subpopulations from a human lung adenocarcinoma cell line. American journal of respiratory cell and molecular biology 17, 353-360.

D'Mello, F., Partidos, C. D., Steward, M. W., and Howard, C. R. (1997). Definition of the primary structure of hepatitis B virus (HBV) pre-S hepatocyte binding domain using random peptide libraries. Virology 237, 319-326.

DeLeo, F. R., Yu, L., Burritt, J. B., Loetterle, L. R., Bond, C. W., Jesaitis, A. J., and Quinn, M. T. (1995). Mapping sites of interaction of p47-phox and flavocytochrome b with random-sequence peptide phage display libraries. Proc Natl Acad Sci USA 92, 7110-7114.

Drummond, D. C., Meyer, O., Hong, K., Kirpotin, D. B., and Papahadjopoulos, D. (1999). Optimizing liposomes for delivery of chemotherapeutic agents to solid tumors. Pharmacological reviews 51, 691-743.

Dvorak, H. F., Nagy, J. A., and Dvorak, A. M. (1991). Structure of solid tumors and their vasculature: implications for therapy with monoclonal antibodies. Cancer Cells 3, 77-85.

Essler, M., and Ruoslahti, E. (2002). Molecular specialization of breast vasculature: a breast-homing phage-displayed peptide binds to aminopeptidase P in breast vasculature. Proc Natl Acad Sci USA 99, 2252-2257.

Folgori, A., Tafi, R., Meola, A., Felici, F., Galfre, G., Cortese, R., Monaci, P., and Nicosia, A. (1994). A general strategy to identify mimotopes of pathological antigens using only random peptide libraries and human sera. Embo J 13, 2236-2243.

Fry, W. A., Phillips, J. L., and Menck, H. R. (1999). Ten-year survey of lung cancer treatment and survival in hospitals in the United States: a national cancer data base report. Cancer 86, 1867-1876.

Fu, Y., Shearing, L. N., Haynes, S., Crewther, P., Tilley, L., Anders, R. F., and Foley, M. (1997). Isolation from phage display libraries of single chain variable fragment antibodies that recognize conformational epitopes in the malaria vaccine candidate, apical membrane antigen-1. J Biol Chem 272, 25678-25684.

Gabizon, A., and Papahadjopoulos, D. (1988). Liposome formulations with prolonged circulation time in blood and enhanced uptake by tumors. Proceedings of the National Academy of Sciences of the United States of America 85, 6949-6953.

Gregoriadis, G., Wills, E. J., Swain, C. P., and Tavill, A. S. (1974). Drug-carrier potential of liposomes in cancer chemotherapy. Lancet 1, 1313-1316.

Hall, B. L., Boroughs, J., and Kobrin, B. J. (1998). A novel tumor-specific human single-chain Fv selected from an active specific immunotherapy phage display library. Immunotechnology 4, 127-140.

Hashizume, H., Baluk, P., Morikawa, S., McLean, J. W., Thurston, G., Roberge, S., Jain, R. K., and McDonald, D. M. (2000). Openings between defective endothelial cells explain tumor vessel leakiness. Am J Pathol 156, 1363-1380.

Herbst, R. S., and Sandler, A. B. (2004). Overview of the current status of human epidermal growth factor receptor inhibitors in lung cancer. Clin Lung Cancer 6 Suppl 1, S7-S19.

Hu, W., and Kavanagh, J. J. (2003). Anticancer therapy targeting the apoptotic pathway. Lancet Oncol 4, 721-729.

Huang, S. K., Mayhew, E., Gilani, S., Lasic, D. D., Martin, F. J., and Papahadjopoulos, D. (1992). Pharmacokinetics and therapeutics of sterically stabilized liposomes in mice bearing C-26 colon carcinoma. Cancer research 52, 6774-6781.

Ihde, D. C. (1992). Chemotherapy of lung cancer. The New England journal of medicine 327, 1434-1441.

Jain, R. K. (1996). Delivery of molecular medicine to solid tumors. Science 271, 1079-1080.

Jain, R. K. (1997). The Eugene M. Landis Award Lecture 1996. Delivery of molecular and cellular medicine to solid tumors. Microcirculation 4, 1-23.

Jemal, A., Thomas, A., Murray, T., and Thun, M. (2002). Cancer statistics, 2002. CA: a cancer journal for clinicians 52, 23-47.

Kelly, K., Crowley, J., Bunn, P. A., Jr., Presant, C. A., Grevstad, P. K., Moinpour, C. M., Ramsey, S. D., Wozniak, A. J., Weiss, G. R., Moore, D. F., et al. (2001). Randomized phase III trial of paclitaxel plus carboplatin versus vinorelbine plus cisplatin in the treatment of patients with advanced non-small-cell lung cancer: a Southwest Oncology Group trial. J Clin Oncol 19, 3210-3218.

Klibanov, A. L., Maruyama, K., Torchilin, V. P., and Huang, L. (1990). Amphipathic polyethyleneglycols effectively prolong the circulation time of liposomes. FEBS letters 268, 235-237.

Koivunen, E., Arap, W., Rajotte, D., Lahdenranta, J., and Pasqualini, R. (1999). Identification of receptor ligands with phage display peptide libraries. J Nucl Med 40, 883-888.

Kraft, S., Diefenbach, B., Mehta, R., Jonczyk, A., Luckenbach, G. A., and Goodman, S. L. (1999). Definition of an unexpected ligand recognition motif for alphav beta6 integrin. J Biol Chem 274, 1979-1985.

Lee, T. Y., Wu, H. C., Tseng, Y. L., and Lin, C. T. (2004). A novel peptide specifically binding to nasopharyngeal carcinoma for targeted drug delivery. Cancer Res 64, 8002-8008.

Levy, S. E., and Hyman, S. L. (2005). Novel treatments for autistic spectrum disorders. Mental retardation and developmental disabilities research reviews 11, 131-142.

Li, B., Tom, J. Y., Oare, D., Yen, R., Fairbrother, W. J., Wells, J. A., and Cunningham, B. C. (1995). Minimization of a polypeptide hormone. Science 270, 1657-1660.

Lin, C. T., Wong, C. I., Chan, W. Y., Tzung, K. W., Ho, J. K., Hsu, M. M., and Chuang, S. M. (1990). Establishment and characterization of two nasopharyngeal carcinoma cell lines. Laboratory investigation; a journal of technical methods and pathology 62, 713-724.

Liu, I. J., Hsueh, P. R., Lin, C. T., Chiu, C. Y., Kao, C. L., Liao, M. Y., and Wu, H. C. (2004). Disease-specific B Cell epitopes for serum antibodies from patients with severe acute respiratory syndrome (SARS) and serologic detection of SARS antibodies by epitope-based peptide antigens. J Infect Dis 190, 797-809.

Lopes de Menezes, D. E. K., M. J.; Gagne, J.-F.; Pilarski, L. M.; Allen, T. M. (1999). Cellular Trafficking and Cytotoxicity of Anti-CD19-Targeted Liposomal Doxorubicin in B Lymphoma Cells. J Liposome Res 9, 199-228.

Lynch, T. J., Adjei, A. A., Bunn, P. A., Jr., DuBois, R. N., Gandara, D. R., Giaccone, G., Govindan, R., Herbst, R. S., Johnson, B. E., Khuri, F. R., et al. (2004). Novel agents in the treatment of lung cancer: conference summary statement. Clin Cancer Res 10, 4199s-4204s.

Mantyh, P. W. (2006). Cancer pain and its impact on diagnosis, survival and quality of life. Nat Rev Neurosci 7, 797-809.

Matsumura, Y., and Maeda, H. (1986). A new concept for macromolecular therapeutics in cancer chemotherapy: mechanism of tumoritropic accumulation of proteins and the antitumor agent smancs. Cancer research 46, 6387-6392.

Mazzucchelli, L., Burritt, J. B., Jesaitis, A. J., Nusrat, A., Liang, T. W., Gewirtz, A. T., Schnell, F. J., and Parkos, C. A. (1999). Cell-specific peptide binding by human neutrophils. Blood 93, 1738-1748.

Neumeister, P., Eibl, M., Zinke-Cerwenka, W., Scarpatetti, M., Sill, H., and Linkesch, W. (2001). Hepatic veno-occlusive disease in two patients with relapsed acute myeloid leukemia treated with anti-CD33 calicheamicin (CMA-676) immunoconjugate. Annals of hematology 80, 119-120.

Nord, K., Gunneriusson, E., Ringdahl, J., Stahl, S., Uhlen, M., and Nygren, P. A. (1997). Binding proteins selected from combinatorial libraries of an alpha-helical bacterial receptor domain. Nat Biotechnol 15, 772-777.

Northfelt, D. W., Martin, F. J., Working, P., Volberding, P. A., Russell, J., Newman, M., Amantea, M. A., and Kaplan, L. D. (1996). Doxorubicin encapsulated in liposomes containing surface-bound polyethylene glycol: pharmacokinetics, tumor localization, and safety in patients with AIDS-related Kaposi's sarcoma. J Clin Pharmacol 36, 55-63.

Ostoros, G., Kovacs, G., Szondy, K., and Dome, B. (2005). [New therapies for non-small cell lung cancer]. Orvosi hetilap 146, 1135-1141.

Papahadjopoulos, D., Allen, T. M., Gabizon, A., Mayhew, E., Matthay, K., Huang, S. K., Lee, K. D., Woodle, M. C., Lasic, D. D., Redemann, C., and et al. (1991). Sterically stabilized liposomes: improvements in pharmacokinetics and antitumor therapeutic efficacy. Proceedings of the National Academy of Sciences of the United States of America 88, 11460-11464.

Park, J. W., Hong, K., Kirpotin, D. B., Colbern, G., Shalaby, R., Baselga, J., Shao, Y., Nielsen, U. B., Marks, J. D., Moore, D., et al. (2002). Anti-HER2 immunoliposomes: enhanced efficacy attributable to targeted delivery. Clin Cancer Res 8, 1172-1181.

Parkin, D. M., Bray, F. I., and Devesa, S. S. (2001). Cancer burden in the year 2000. The global picture. Eur J Cancer 37 Suppl 8, S4-66.

Pasqualini, R., Koivunen, E., and Ruoslahti, E. (1995). A peptide isolated from phage display libraries is a structural and functional mimic of an RGD-binding site on integrins. J Cell Biol 130, 1189-1196.

Pasqualini, R., and Ruoslahti, E. (1996). Organ targeting in vivo using phage display peptide libraries. Nature 380, 364-366.

Prezzi, C., Nuzzo, M., Meola, A., Delmastro, P., Galfre, G., Cortese, R., Nicosia, A., and Monaci, P. (1996). Selection of antigenic and immunogenic mimics of hepatitis C virus using sera from patients. J Immunol 156, 4504-4513.

Ramalingam, S. (2005). First-line chemotherapy for advanced-stage non-small-cell lung cancer: focus on docetaxel. Clin Lung Cancer 7 Suppl 3, S77-82.

Rosenkilde, M. M., and Schwartz, T. W. (2004). The chemokine system—a major regulator of angiogenesis in health and disease. Apmis 112, 481-495.

Ruoslahti, E. (2002). Specialization of tumour vasculature. Nat Rev Cancer 2, 83-90.

Sapra, P., and Allen, T. M. (2004). Improved outcome when B-cell lymphoma is treated with combinations of immunoliposomal anticancer drugs targeted to both the CD19 and CD20 epitopes. Clin Cancer Res 10, 2530-2537.

Schiller, J. H. (2001). Current standards of care in small-cell and non-small-cell lung cancer. Oncology 61 Suppl 1, 3-13.

Scott, J. K., and Smith, G. P. (1990). Searching for peptide ligands with an epitope library. Science 249, 386-390.

Senior, J., Delgado, C., Fisher, D., Tilcock, C., and Gregoriadis, G. (1991). Influence of surface hydrophilicity of liposomes on their interaction with plasma protein and clearance from the circulation: studies with poly(ethylene glycol)-coated vesicles. Biochimica et biophysica acta 1062, 77-82.

Senior, J. H. (1987). Fate and behavior of liposomes in vivo: a review of controlling factors. Critical reviews in therapeutic drug carrier systems 3, 123-193.

Shockley, T. R., Lin, K., Nagy, J. A., Tompkins, R. G., Dvorak, H. F., and Yarmush, M. L. (1991). Penetration of tumor tissue by antibodies and other immunoproteins. Annals of the New York Academy of Sciences 618, 367-382.

Smith, W. C., McDowell, J. H., Dugger, D. R., Miller, R., Arendt, A., Popp, M. P., and Hargrave, P. A. (1999). Identification of regions of arrestin that bind to rhodopsin. Biochemistry 38, 2752-2761.

Thomas, G. E., Esteban, J. M., Raubitschek, A., and Wong, J. Y. (1995). gamma-Interferon administration after 90yttrium radiolabeled antibody therapy: survival and hematopoietic toxicity studies. International journal of radiation oncology, biology, physics 31, 529-534.

Thongprasert, S., Sanguanmitra, P., Juthapan, W., and Clinch, J. (1999). Relationship between quality of life and clinical outcomes in advanced non-small cell lung cancer: best supportive care (BSC) versus BSC plus chemotherapy. Lung Cancer 24, 17-24.

Weinstein, J. N. (1984). Liposomes as drug carriers in cancer therapy. Cancer treatment reports 68, 127-135.

Wong, C., Waibel, R., Sheets, M., Mach, J. P., and Finnern, R. (2001). Human scFv antibody fragments specific for the epithelial tumour marker MUC-1, selected by phage display on living cells. Cancer Immunol Immunother 50, 93-101.

Woodle, M. C., and Lasic, D. D. (1992). Sterically stabilized liposomes. Biochimica et biophysica acta 1113, 171-199.

Wrighton, N. C., Farrell, F. X., Chang, R., Kashyap, A. K., Barbone, F. P., Mulcahy, L. S., Johnson, D. L., Barrett, R. W., Jolliffe, L. K., and Dower, W. J. (1996). Small peptides as potent mimetics of the protein hormone erythropoietin. Science 273, 458-464.

Wu, H. C., Huang, Y. L., Chao, T. T., Jan, J. T., Huang, J. L., Chiang, H. Y., King, C. C., and Shaio, M. F. (2001). Identification of B-cell epitope of dengue virus type 1 and its application in diagnosis of patients. J Clin Microbiol 39, 977-982.

Wu, H. C., Jung, M. Y., Chiu, C. Y., Chao, T. T., Lai, S. C., Jan, J. T., and Shaio, M. F. (2003). Identification of a dengue virus type 2 (DEN-2) serotype-specific B-cell epitope and detection of DEN-2-immunized animal serum samples using an epitope-based peptide antigen. J Gen Virol 84, 2771-2779.

Wu, N. Z., Da, D., Rudoll, T. L., Needham, D., Whorton, A. R., and Dewhirst, M. W. (1993). Increased microvascular permeability contributes to preferential accumulation of Stealth liposomes in tumor tissue. Cancer research 53, 3765-3770.

Yuan, F., Leunig, M., Huang, S. K., Berk, D. A., Papahadjopoulos, D., and Jain, R. K. (1994). Microvascular permeability and interstitial penetration of sterically stabilized (stealth) liposomes in a human tumor xenograft. Cancer Res 54, 3352-3356.

Zalipsky, S., Mullah, N., Harding, J. A., Gittelman, J., Guo, L., and DeFrees, S. A. (1997). Poly(ethylene glycol)-grafted liposomes with oligopeptide or oligosaccharide ligands appended to the termini of the polymer chains. Bioconjugate chemistry 8, 111-118.

DEFINITIONS

The terms used herein have their ordinary meanings, as set forth below, and can be further understood in the context of the specification.

The terms "polynucleotide," "nucleotide," "nucleic acid," "nucleic acid molecule," "nucleic acid sequence," "polynucleotide sequence," and "nucleotide sequence" are used interchangeably herein to refer to polymeric forms of nucleotides of any length. The polynucleotides can contain deoxyribonucleotides, ribonucleotides, and/or their analogs or derivatives. Nucleotide sequences shown herein are listed in the 5' to 3' direction.

The terms "polypeptide," "peptide," and "protein," used interchangeably herein, refer to a polymeric form of amino acids of any length, which can include naturally-occurring amino acids, coded and non-coded amino acids, chemically or biochemically modified, derivatized, or designer amino acids, amino acid analogs, peptidomimetics, and depsipeptides, and polypeptides having modified, cyclic, bicyclic, depsicyclic, or depsibicyclic peptide backbones. The term includes single chain protein as well as multimers. The term also includes proteins conjugated to a label such as FITC, biotin, and radioisotopes, including, but not limited to $^{64}$Cu, $^{67}$Cu, $^{90}$Y, $^{99}$mTc, $^{111}$In, $^{124}$I, $^{125}$I, $^{131}$I, $^{137}$Cs, $^{186}$Re $^{211}$At, $^{212}$Bi, $^{213}$Bi, $^{223}$Ra, $^{241}$Am, and $^{244}$Cm; enzymes having detectable products (for example, luciferase, peroxidase, alkaline phosphatase, β-galactosidase, and the like); fluorescers, and fluorescent labels, fluorescence emitting metals, for example, $^{152}$Eu, or others of the lanthanide series, electrochemiluniescent compounds, chemiluminescent compounds, for example, luminol, isoluminol, or acridinium salts; specific binding molecules, for example, magnetic particles, microspheres, nanospheres, and the like. The term also includes peptides conjugated to therapeutic agents.

The term also includes fusion proteins, including, but not limited to, glutathione S-transferase (GST) fusion proteins, fusion proteins with a heterologous amino acid sequence such as bioluminescent proteins, for example, luciferin, or aequorin (green fluorescent protein), with heterologous and homologous leader sequences, fusion proteins with or without N-terminal methionine residues, pegylated proteins, and immunologically tagged, or his-tagged proteins. Such fusion proteins also include fusions to epitopes. Such fusion proteins can comprise multimers of the peptides of the invention, e.g. homodimers or homomultimers, and heterodimers and heteromultimers. The term also includes peptide aptamers.

Peptides of the invention include biologically active variants of the peptides, where such variants are substantially similar in structure. Variants of polypeptide sequences may include insertions, additions, deletions, or substitutions compared with the subject polypeptides. Variants of polypeptide sequences include biologically active polymorphic variants.

Peptides of the invention can include naturally-occurring and non-naturally occurring amino acids. Peptides can comprise D-amino acids, a combination of D- and L-amino acids, and various "designer" or "synthetic" amino acids (for example, β-methyl amino acids, Ca-methyl amino acids, and Na-methyl amino acids, etc.) to convey special properties. Additionally, peptides can be cyclic. Peptides can include non-classical amino acids in order to introduce particular conformational motifs. Any known non-classical amino acid can be used. Amino acid analogs and peptidomimetics can be incorporated into a peptide to induce or favor specific secondary structures, including, but not limited to, LL-Acp (LL-3-amino-2-propenidone-6-carboxylic acid), a β-turn inducing dipeptide analog; β-sheet inducing analogs; β-turn inducing analogs; α-helix inducing analogs; γ-turn inducing analogs; Gly-Ala turn analogs; amide bond isostere; or tretrazol, and the like.

A desamino or descarboxy residue can be incorporated at the terminal ends of the peptide, so that there is no terminal amino or carboxyl group, to decrease susceptibility to proteases or to restrict conformation. C-terminal functional groups include amide, amide lower alkyl, amide di(lower alkyl), lower alkoxy, hydroxy, and carboxy, and the lower ester derivatives thereof, and the pharmaceutically acceptable salts thereof.

The term "liposome" refers to a composition comprising an outer lipid bi-layer or multi-layer membrane surrounding an internal aqueous space. The term includes multilamellar liposomes, which generally have a diameter in the range of about one to about ten micrometers and comprise anywhere from two to hundreds of concentric lipid bilayers alternating with layers of an aqueous phase. The term includes unilamellar vesicles which are comprised of a single lipid layer and generally have a diameter in the range of about 20 to about 400 nanometers (nm), about 50 to about 300 nm, about 300 to about 400 nm, or about 100 to about 200 nm. The term also includes liposomes with diameters from about 65 nm to about 75 nm.

The terms "antibody" and "immunoglobulin" refer to a protein, for example, one generated by the immune system, synthetically, or recombinantly, that is capable of recognizing and binding to a specific antigen. Antibodies are commonly known in the art, and can be prepared by methods known in the art.

An "epitope" is a molecule to which an antibody binds, which may or may not be a contiguous sequence of amino acid residues in a polypeptide, and which may comprise sugars and/or molecules having other chemical structures.

The term "binds specifically," in the context of a polynucleotide, refers to hybridization under stringent conditions. Conditions that increase stringency of both DNA/DNA and DNA/RNA hybridization reactions are widely known and published in the art. Examples of stringent hybridization conditions include hybridization in 4× sodium chloride/sodium citrate (SSC), at about 65-70° C., or hybridization in 4×SSC plus 50% formamide at about 42-50° C., followed by one or more washes in 1×SSC, at about 65-70° C.

The term "ligand" refers to a molecule that binds to another molecule, including a receptor.

A "host cell" is an individual cell or cell culture which can be or has been a recipient of any recombinant vector(s) or isolated polynucleotide. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the invention. A host cell which comprises a recombinant vector of the invention may be called a "recombinant host cell."

A "specimen" is any biological specimen derived from a patient; the term includes, but is not limited to, biological fluids such as blood, serum, plasma, urine, cerebrospinal fluid, tears, saliva, lymph, dialysis fluid, lavage fluid, semen, and other liquid samples, as well as cell and tissues of biological origin. The term also includes cells or cells derived therefrom and the progeny thereof, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. This definition encompasses samples that have been manipulated in any way after their procurement, such as by treatment with reagents, solubilization, or enrichment for certain components, such as polynucleotides or polypeptides. Also included in the term are derivatives and fractions of patient samples. A patient sample may be used in a diagnostic, prognostic, or other monitoring assay. The specimen can be from a human patient or a non-human mammal.

"Treatment," as used herein, covers any administration or application of remedies for disease in a mammal, including a human, and includes inhibiting the disease, arresting its development, or relieving the disease, for example, by causing regression, or restoring or repairing a lost, missing, or defective function; or stimulating an inefficient process. The term includes obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse affect attributable to the disorder. Thus, the invention provides both treatment and prophylaxis. It includes (1) preventing the disorder from occurring or recurring in a subject who may be predisposed to the disorder but is not yet symptomatic, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, and/or tumor size.

A "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

A "pharmaceutical composition" herein refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses, or powders.

"Disease" refers to any condition, infection, disorder, or syndrome that requires medical intervention or for which medical intervention is desirable. Such medical intervention can include treatment, diagnosis, and/or prevention.

"Cancer" is any abnormal cell or tissue growth, for example, a tumor, whether malignant, pre-malignant, or non-malignant. It is characterized by uncontrolled proliferation of cells that may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more neoplastic cell type. The term cancer includes lung cancer, colon cancer, breast cancer, prostate cancer, liver cancer, pancreatic cancer, and oral cancer.

Cell Lines

Useful cell lines include A549, human lung squamous cell carcinoma line, CL1-5, high metastatic human lung adenocarcinoma line, H23, human lung adenocarcinoma line, H460, human lung large cell carcinoma line, PC13, human lung cancer line, NPC-TW01, human nasopharyngeal carcinoma line, SAS, human oral squamous cell carcinoma line, PaCa, human pancreas carcinoma, NNM, human normal nasal mucosal epithelia, and fibroblast. A549, H23, H460, PC13, PaCa, and SAS are available from the American Type Culture Collection. CL1-5 and NPC-TW01 cell lines were established by (Chu et al., 1997) and (Lin et al., 1990), respectively.

Preparation of Peptides

The peptides of the invention can be expressed using methods known in the art. Cell-based methods and cell-free methods are suitable for producing peptides of the invention. Cell-based methods generally involve introducing a nucleic acid construct into a host cell in vitro and culturing the host cell under conditions suitable for expression, then harvesting the peptide, either from the culture medium or from the host cell, (for example, by disrupting the host cell), or both. The invention also provides methods of producing a peptide using cell-free in vitro transcription/translation methods, which are well known in the art.

Suitable host cells include prokaryotic or eukaryotic cells, including, for example, bacterial, yeast, fungal, plant, insect, and mammalian cells.

Typically, a heterologous peptide, whether modified or unmodified, may be expressed on its own, as described above, or as a fusion protein, and may include not only secretion signals, but also a secretory leader sequence. A secretory leader sequence of the invention may direct certain proteins to the ER. The ER separates the membrane-bound proteins from other proteins. Once localized to the ER, proteins can be further directed to the Golgi apparatus for distribution to vesicles; including secretory vesicles; the plasma membrane, lysosomes, and other organelles.

Additionally, peptide moieties and/or purification tags may be added to the peptides. Such regions may be removed prior to final preparation of the polypeptide. The addition of peptide moieties to polypeptides to engender secretion or excretion, to improve stability, and to facilitate purification, among other reasons, are familiar and routine techniques in the art. Suitable purification tags include, for example, V5, polyhistidines, avidin, and biotin. Conjugation of peptides to compounds such as biotin can be accomplished using techniques well known in the art. (Hermanson ed. (1996) Bioconjugate Techniques; Academic Press). Peptides can also be conjugated with radioisotopes, toxins, enzymes, fluorescent labels, colloidal gold, nucleic acids, vinorelbine, and doxorubicin using techniques known in the art. (Hermanson ed. (1996) Bioconjugate Techniques; Academic Press; Stefano et al. (2006) A conjugate of doxorubicin with lactosaminated albumin enhances the drug concentrations in all the forms of rat hepatocellular carcinomas independently of their differentiation grade. Liver Int. 26:726-33). Toxins those known in the art. Kreitman and Pastan, Immunotoxins in the treatment of hematologic malignancies. Curr Drug Targets. 7:1301-11 (2006).

Fusion partners suitable for use in the invention include, for example, fetuin, human serum albumin, Fc, and/or one or more of their fragments. Conjugated proteins, such as polyethylene glycol conjugates, are also provided.

The peptides of the invention can also be chemically synthesized using techniques known in the art (e.g., see Hunkapiller et al., Nature, 310:105 111 (1984); Grant ed.

(1992) Synthetic Peptides, A Users Guide, W.H. Freeman and Co.; U.S. Pat. No. 6,974,884)). For example, a polypeptide corresponding to a fragment of a polypeptide can be synthesized by use of a peptide synthesizer or through the use of solid-phase methods known in the art.

Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The polypeptides of the invention can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

A peptide or peptidomimetic of the invention can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran, and dextran derivatives. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in (Zallipsky, S. (1995) Bioconjugate Chem., 6:150-165; Monfardini, C., et al. (1995) Bioconjugate Chem. 6:62-69; U.S. Pat. Nos. 4,640,835; 4,496,689; 4,301,144; 4,670,417; 4,791,192, 4,179,337, or WO 95/34326).

Preparation of Liposomes

A variety of methods for preparing liposomes are known in the art, several of which are described by Lichtenberg and Barenholz in Methods of Biochemical Analysis, Volume 33, 337-462 (1988). Small unilamellar vesicles (SUV, size <100 nm) can be prepared by a combination of standard methods of thin-film hydration and repeated extrusion as described before (Tseng et al., 1999). Preparation methods particularly involving the encapsulation of DNA by liposomes, and methods that have a direct application to liposome-mediated transfection, have been described by Hug and Sleight et al (1991). Methods of making liposomes are also disclosed in U.S. Pat. No. 6,355,267 and U.S. Pat. No. 6,663,885. Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

Liposomes are also commercially available from sources such as the Taiwan Liposome Company, Taipei Taiwan. Additional commercially available liposomes include TLC-D99, Lipo-Dox, Doxil, DaunoXome, AmBisome, ABELCET, transfectace (DDAB/DOPE), and DOTAP/DOPE and Lipofectin.

The liposomes of the present invention are most frequently prepared from phospholipids, but other molecules of similar molecular shape and dimensions having both a hydrophobic and a hydrophilic moiety can be used. For the purposes of the present invention, all such suitable liposome-forming molecules will be referred to herein as lipids. One or more naturally occurring and/or synthetic lipid compounds may be used in the preparation of the liposomes.

Liposomes may be anionic, cationic, or neutral depending upon the choice of the hydrophilic group. For instance, when a compound with a phosphate or a sulfate group is used, the resulting liposomes will be anionic. When amino-containing lipids are used, the liposomes will have a positive charge, and will be cationic liposomes.

Representative suitable phospholipids or lipid compounds for forming initial liposomes useful in the present invention include, but are not limited to, phospholipid-related materials such as phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol. Additional nonphosphorous-containing lipids include, but are not limited to, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, diacylglycerolsuccinate, and the like.

Liposomal preparations for use in the instant invention include cationic (positively charged), anionic (negatively charged), and neutral preparations.

Remote loading of compounds into liposomes employs formation of transmembrane gradients (Ceh and Lasic, 1995). This method includes incubating the compound to be loaded into the liposomes and a boronic acid compound with suspended liposomes, thereby achieving accumulation of the compound within the liposomes (Ceh B. and Lasic D. D., 1995; U.S. Pat. No. 6,051,251).

A phosphate assay can be used to determine liposome concentration. One phosphate assay is based on the interaction between molybdate and malachite green dye. The main principle involves the reaction of inorganic phosphate with molybdate to form a colorless unreduced phosphomolybdate complex which is converted to a blue colored complex when reduced under acidic conditions. Phosphomolybdate gives 20 or 30 times more color when complexed with malachite green. The final product, reduced green soluble complex is measured by its absorbance at 620 nm and is a direct measure of inorganic phosphate in solution.

In some embodiments, the liposomes are provided in formulation with pharmaceutically acceptable carriers, excipients, and diluents, of which a wide variety are known in the art. These pharmaceutical carriers, excipients, and diluents include those listed in the USP pharmaceutical excipients listing. USP and NF Excipients, Listed by Categories, p. 2404-2406, USP 24 NF 19, United States Pharmacopeial Convention Inc., Rockville, Md. (ISBN 1-889788-03-1). Pharmaceutically acceptable excipients, such as vehicles, adjuvants, carriers, or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable carriers include, but are not limited to, water, dextrose, glycerol, saline, ethanol, and combinations thereof. The carrier can contain additional agents such as wetting or emulsifying agents, pH buffering agents, or adjuvants which enhance the effectiveness of the formulation. Topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents can be added as necessary. Percutaneous penetration enhancers such as Azone can also be included.

In pharmaceutical dosage forms, the compositions of the invention can be administered in the form of their pharmaceutically acceptable salts, or they can also be used alone or in appropriate association, as well as in combination, with other pharmaceutically active compounds. The subject compositions are formulated in accordance to the mode of potential administration.

Methods of Treatment

Peptides or liposomes of the invention comprising therapeutic drugs may be administered to a subject in need of treatment by injection systemically, such as by intravenous injection; or by injection or application to the relevant site, such as by direct injection into a tumor, or direct application to the site when the site is exposed in surgery; or by topical application, such as if the disorder is on the skin, for example.

Peptides or liposomes of the invention can be used as monotherapy. Alternatively, the peptides or liposomes of the invention can be used in combination with standard chemotherapeutic or radiation regimens to treat cancers.

The peptides of the invention could be used to target antibodies to cancer cells for treatment. In one embodiment, a peptide of the invention is administered to a subject in need of treatment, followed by administration of an antibody that binds specifically to the peptide. The targeted antibodies may mediate antibody-dependent cell cytotoxicity or complement-dependent cytotoxicity, or may modify the underlying function of the target molecule. Such antibodies can be used in the form of antibody conjugates to directly deliver agents with a therapeutic effect on the target tissue. Such agents include radionuclides, toxins, chemotherapeutics, and anti-angiogenic compounds.

Administration of the agents can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Thus, the subject compositions can be formulated into preparations in solid, semi-solid, liquid or gaseous forms, such as tablets, capsules, powders, granules, ointments, solutions, suppositories, injections, inhalants, and aerosols. The following methods and excipients are merely exemplary and are in no way limiting.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art. The composition or formulation to be administered will, in any event, contain a quantity of the agent adequate to achieve the desired state in the subject being treated.

The liposomes or peptides of the invention can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers, and preservatives. Other formulations for oral or parenteral delivery can also be used, as conventional in the art.

The liposomes or peptides of the invention may comprise one or more of the wide variety of drugs that have been employed in cancer treatment and inhibition of angiogenesis, including, but are not limited to, vinorelbine, cisplatin, gemcitabine, paclitaxel, etoposide, Novantrone (mitoxantrone), actinomycin D, camptohecin (or water soluble derivatives thereof), methotrexate, mitomycins (for example, mitomycin C), dacarbazine (DTIC), cyclophosphamide, and anti-neoplastic antibiotics such as doxorubicin and daunomycin, or others, described, for example, in De Vita et al., 2001. The liposomes or peptides can also comprise cytotoxic drugs, oligonucleotides, toxins, and radioactive molecules. The liposomes or peptides may also comprise compounds such as anti-VEGF aptamers described in (Ng et al. 2006).

Drugs employed in cancer therapy may have a cytotoxic or cytostatic effect on cancer cells, or may reduce proliferation of the malignant cells. Drugs employed in cancer treatment can also be peptides. A liposome or peptide of the invention can be combined with radiation therapy. A liposome or peptide of the invention may be used adjunctively with therapeutic approaches described in (De Vita, et al., (2001)). For those combinations in which a liposome or peptide of the invention and a second anti-cancer agent exert a synergistic effect against cancer cells, the dosage of the second agent may be reduced, compared to the standard dosage of the second agent when administered alone. A method for increasing the sensitivity of cancer cells comprises co-administering a liposome or peptide of the invention with an amount of a chemotherapeutic anti-cancer drug that is effective in enhancing sensitivity of cancer cells. Co-administration may be simultaneous or non-simultaneous administration. A liposome or peptide of the invention may be administered along with other therapeutic agents, during the course of a treatment regimen. In one embodiment, administration of a liposome or peptide of the invention and other therapeutic agents is sequential. An appropriate time course may be chosen by the physician, according to such factors as the nature of a patient's illness and the patient's condition.

Diagnostic Methods

Detection of disease-specific biomarkers provides an effective screening strategy. Early detection provides not only early diagnosis, but in the case of cancer, can provide the ability to screen for polymorphism and detect post-operative residual tumor cells and occult metastases, an early indicator of tumor recurrence. Early detection of disease-specific biomarkers can thus improve survival in patients before diagnosis, while undergoing treatment, and while in remission.

The peptides of the invention can be used as a diagnostic or prognostic for diseases. The peptides can be used as diagnostics in a number of ways, including but not limited to ELISA, Western blot, fluorescence, immunofluorescence, immunohistochemistry, or autoradiography.

The antibodies of the present invention can also be used in combination with the peptides of the invention to detect cancer. In some embodiments, the assay is a binding assay that detects binding of an antibody with a peptide of the invention that has bound cancer cell. The subject polypeptide or antibody can be immobilized, while the subject polypeptide and/or antibody can be detectably labeled. For example, the antibody can be directly labeled or detected with a labeled secondary antibody. That is, suitable detectable labels for antibodies include direct labels, which label the antibody to the protein of interest, and indirect labels, which label an antibody that recognizes the antibody to the protein of interest. In another embodiment, the peptide comprises a label, and the binding of the peptide to a tissue is detected by assaying for the presence of the label.

Screening Methods

The invention provides a methods for identifying biological ligands that bind to peptides of the invention.

In one method, the peptides of the invention can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Suter et al. (2006) Biotechniques 40:625-44 to identify other proteins, which bind to or interact with peptides of the invention.

In another method, peptides of the invention are incubated with cellular extracts and molecules that bind to peptides of the invention are identified. In one method, the peptides of the invention are immobilized on a solid support, such as an HPLC column, and cellular extracts are exposed to immobilized peptides under conditions facilitating the binding of the peptides of the invention to target molecules. Bound molecules are eluted and identified through standard techniques such as mass-spectrometry.

Affinity Purification of Target Protein

Proteins are extracted from lung cancer cells at 4° C. for 30 min with lysis buffer (50 mM Tris-HCl, pH 7.4, 150 mM NaCl, 30 μg/ml DNase, 1% Nonidet P-40, and protease inhibitors (Complete tabs; Roche Molecular Biochemicals). Protein lysates are cleared of debris by centrifugation at 15,000×g for 20 min. The lysates are first precleared on a 1-ml column containing control peptide, and the flow-through is directly applied onto a second 1-ml column of SP5-52 or SP5-2 peptide-immobilized affinity column. Columns are washed and eluted. The purity of the isolated protein is monitored by SDS-PAGE (8% polyacrylamide) and visualized by silver staining. The desired protein bands are cut out from the gel for in-gel digestion with trypsin. The resultant polypeptides are further analyzed by mass spectrometry.

EXAMPLES

The examples, which are intended to be purely exemplary of the invention and should therefore not be considered to limit the invention in any way, also describe and detail aspects and embodiments of the invention discussed above.

Example 1

Phage-Display Biopanning

A549, CL1-5, H23, and H460 cells were grown in RPMI 1640 supplemented with 2 g bicarbonate, 40 mg kanamycin per liter, 2 mM L-glutamine, and 10% fetal bovine serum at 37° C. under a humidified atmosphere of 95% air and 5% $CO_2$ (v/v). NPC-TW01, PC13, SAS, PaCa, NNM, and fibroblast were grown in DMEM containing 3.7 g bicarbonate, 40 mg kanamycin per liter, 2 mM L-glutamine, and 10% fetal bovine serum at 37° C. under a humidified atmosphere of 90% air and 10% CO2 (v/v).

NSCLC, CL1-5, cells were washed with the serum free RPMI and then blocked with blocking buffer (serum free RPMI containing 1% BSA) at 4° C. for 30 minutes. The cells were incubated with UV-treated inactive control helper phage (insertless phage) at 4° C. for 1 h. After inhibition of nonspecific binding, a phage displayed peptide library (New England BioLabs, Mass., USA) was added and incubated at 4° C. for 1 h. The bound phages were eluted with lysis buffer (150 mM NaCl, 50 mM Tris-HCl pH 8.0, 1 mM EDTA pH 7.5, 1% NP-40, 0.5% Sodium deoxycholate, 0.1% SDS) on ice. This eluted phage pool was amplified and titered in *Escherichia coli* ER2738 culture (New England BioLabs, Mass., USA). The recovered phages were used as input for subsequent rounds of panning. The eluted phages, following the fifth round of selection, were titered on LB/IPTG/X-Gal plates. For phage titering, 5 ml of LB was inoculated with a single colony of ER 2738 and incubated with shaking until mid-log phase ($OD_{600}$~0.5). Once the culture had reached mid-log phase, 200 μl of culture was dispensed into microfuge tubes in which 10 μl of each dilution was added to each tube, after which the tubes were vortexed quickly and incubated at room temperature for five minutes. The infected cells are transferred one at a time, to a culture tube containing Agarose Top (Cambrex Bio Science Rockland, Inc., ME, USA), mixed quickly, and immediately poured onto a prewarmed LB/IPTG/X-Gal plate.

96-well ELISA plates (Falcon, Calif., USA) were seeded with cancer and control cells, separately. Cells were washed with serum free DMEM and then blocked with blocking buffer. Then, individual phage particles were added to the cell-coated plates and incubated at 4° C. for 2 h, followed by incubation with horseradish peroxidase (HRP)-conjugated mouse anti-M13 monoclonal antibody (Pharmacia, Sweden) and then with the peroxidase substrate o-phenylenediamine dihydrochloride (OPD; Sigma, Germany). The reaction was read using a microplate reader at 490 nm.

Selected phage clones were further analyzed by DNA sequencing. The DNA sequences of purified phages were determined according to the dideoxynucleotide chain termination method using an automated DNA sequencer (ABI PRISM 377, Perkin-Elmer, CA, USA). The sequencing was performed with primer 5'-CCCTCATAGTTAGCGTAACG-3' [SEQ ID NO: 21] corresponding to the pIII gene sequence. The phage-displayed peptide sequences were translated and aligned using Genetics Computer Group (GCG) program.

After four rounds of biopanning, the titer of phage eluted from NSCLC, CL1-5, cells increased to 30-fold relative to the first round, and increased to 40-fold in the fifth round of selection (FIG. 1). Enriched phages from the third to fifth biopanning rounds were randomly selected and sequenced. We also sequenced phage clones with higher CL1-5-binding activity.

The phages PC3-1, PC4-1, PC4-5, PC5-2 and PC5-4 display a consensus motif, Tryptophan (W)-Threonine (T)/Tyrosine (Y)-Tyrosine (Y) (Table 1). Interestingly, PC5-2 appeared in third (PC3-1), fourth (PC4-1), and fifth (PC5-2) biopanning rounds. The frequency of PC5-2 in each biopanning round increased from 20% (⅕) at the third cycle to 90% (²⁷/₃₀) at the fifth cycle (Table 1). We focused on the peptide TDSILRSYDWTY (SP5-2) for further study.

Example 2

Identification of the Phages Binding to Cancer Cells by Immunohistochemistry

To investigate whether PC5-2 could specifically bind to NSCLC cells, we used immunohistochemistry to localize the phage particles in different cell types. All cancer cell lines, NNM and fibroblasts were plated and grown to about 80% confluence on cover slips. The cover slips were incubated in the blocking buffer, treated with 1% hydrogen peroxide plus 0.1% NaN$_3$ to block endogenous peroxidase activity, and then incubated with each selected phage at 4° C. for 1 h. The cover slips were washed and incubated with HRP-labeled mouse anti-M13 monoclonal antibody at 4° C. for 1 h. The slides were fixed with 3% formaldehyde for 10 min, and subjected to peroxidase substrate and mounted with 50% glycerol in PBS.

The results showed that PC5-2 bound specifically to NSCLC cell lines including CL1-5 and PC13 (FIG. 2A, arrows). The control helper phage, which did not display this peptide, could not bind to CL1-5 cells. PC5-2 also could not bind to other cancer cell lines such as oral cancer (SAS) and nasopharyngeal carcinoma cells (NPC-TW01) or to normal epithelial cells from nasal mucosal (NNM) (FIG. 2A). Scale bar: 10 μm.

To investigate whether the synthetic peptide and the selected phage clone competed for the same binding site, a peptide-competitive inhibition assay was performed by immunofluorescent staining. Targeting peptide TDSILRSY-DWTY (SP5-2) [SEQ ID NO: 2] and control peptide (RLL-DTNRPLLPY) [SEQ ID NO: 22] were synthesized and purified by reverse-phase high-performance liquid chromatography to >95% purity by Invitrogene, Inc. (CA, USA). Conjugation of these peptides with FITC or biotin was performed by adding FITC or biotin to the peptide NH$_2$ terminus by the same company.

CL1-5 cells were cultured on cover slips overnight, and then preincubated with UV-treated inactive control phage in blocking solution to block nonspecific binding. Phages were mixed with different concentrations of synthetic peptides and incubated with cells at 4° C. for 1 h. The slides were further incubated with mouse anti-M13 monoclonal antibody (Amersham Biosciences, Uppsala, Sweden), followed by incubation with FITC-labeled goat anti-mouse antibody (Jackson ImmunoResearch). The slides were washed and mounted with mounting medium (Vector, Calif., USA). Then the slides were examined under a Leica Universal microscope. The images were merged by SimplePCI (C-IMAGING, PA, USA) software.

The results showed that the binding activity of CL1-5 cells with the PC5-2 phage was inhibited by SP5-2 synthetic peptide in a dose-dependent manner. 27 μg/ml of SP5-2 was able to inhibit the PC5-2 binding activity completely (FIG. 2B), whereas the control peptide had no such effect. The control phage could not bind to CL1-5 cells and PC5-2 could not bind to NPC-TW01 in this assay (FIG. 2B). Scale bar: 10 μm.

Furthermore, to investigate the target molecule expressed on the cell surface of CL1-5, we measured PC5-2-bound cells using flow cytometry. Lung and other cancer cell lines were cultured overnight and then suspended in PBS containing 50 mM EDTA and blocked with blocking buffer at 4° C. for 30 minutes. The cells were washed 2 times with flow buffer (PBS containing 1% fetal bovine serum). The cells were incubated with phages or FITC-labeled peptide. For the peptide competitive inhibition assay, the phages were mixed with different concentrations of synthetic peptides and the mixture was incubated with the cells. After washing two times with cold flow buffer, the phage-bound cells were incubated with anti-M13 monoclonal antibodies at 4° C. for 1 h and then treated with FITC-conjugated goat anti-mouse IgG antibody. The cells were washed two times with cold flow buffer and then applied to a flow cytometer (Becton Dickinson).

The results showed that 42.6% of CL1-5 cells could be bound by the PC5-2 (FIG. 2C, c) and the bound phage was completely inhibited by the SP5-2 peptide (FIG. 2C, d). PC5-2 could not bind to SAS and normal epithelial cells (NNM) (FIG. 2C, e and f). PC5-2 also could not bind to NPC-TW01 by this assay (FIG. 2C, b). These results indicate that part of CL1-5 cells express an unknown protein or other molecule that could be recognized by the peptide ligand displayed on PC5-2.

Example 3

Binding of Targeting Peptide with NSCLC Cells and Lung Cancer Biopsies

To determine if the peptide sequences displayed on the PC5-2 indeed interacted with the NSCLC cells, we used FITC-labeled SP5-2 peptide in place of the PC5-2 phage for a peptide-binding assay using immunofluorescent staining. The results showed that the FITC-labeled SP5-2 specifically bound to the different NSCLC cell lines including CL1-5, H460, A549, PC13 and H23, but not normal epithelial cells (NNM). The FITC-labeled control peptide revealed no such binding activity (FIG. 3A). Scale bar: 10 μm.

To further confirm FITC-labeled SP5-2 could bind to these NSCLC cell lines, we also measured SP5-2-bound cells using flow cytometry. Samples were prepared as in Example 2. Flow cytometry histograms show the FITC-labeled SP5-2 binding to each NSCLC cell line (blue) and the backgrounds of FITC-labeled control peptide (red). The ratio of binding activity for CL1-5, H460, A549, PC13 and H23 was 43%, 45.8%, 44.3%, 20.1% and 44%, respectively (FIG. 3B). These results revealed that PC5-2 and SP5-2 could target to NSCLC cells.

To further identify whether this targeting ligand has affinity for human lung cancer biopsy specimens, we tested the reactivity of PC5-2 and SP5-2 with pulmonary adenocarcinoma from lung cancer patients by immunohistochemistry. Human lung adenocarcinoma sections were prepared and the slides were incubated in the blocking buffer for 30 min, and then treated with 3% hydrogen peroxide plus 0.1% NaN$_3$ in methanol to block endogenous peroxidase activity, and incubated with phage clones or biotin-labeled peptide. PC5-2 was detected using HRP-conjugated anti-M13 antibody using routine immunohistochemical staining.

The results revealed that both PC5-2 and biotin-labeled SP5-2 could recognize the tumor cells in NSCLC biopsy specimens (FIG. 3C, a and b, arrows). However, the control phage and biotin-labeled control peptide could not bind to NSCLC biopsy specimens (FIG. 3C, c and d). These data indicate that SP5-2 recognized an unknown molecule expressed on NSCLC cell lines and cancer cells from lung cancer patients. Scale bar: 25 μm.

Example 4

Verification of Tumor-Homing Ability of PC5-2 in vivo

To investigate the targeting ability of PC5-2 in vivo, phages were injected into the tail vein of mice bearing CL1-5-derived tumors and recovered after perfusion. SCID mice were injected subcutaneously into the dorsolateral flank with 1×10$^7$ cancer cells. The mice bearing size-matched lung cancer-derived tumor (tumor sizes about 500 mm3) were injected with targeting phage or control phage through the tail vein. Eight minutes after injection, the mice were treated with diethyl ether to drive them into deep anesthesia. Then the mice were perfused with 50 ml PBS to wash unbound phage. The control organs (brain, heart, and lung) and tumor mass were removed, weighed, and washed three times with cold PBS-PI (protease inhibitor cocktail tablet; Roche, Germany). The organ and tumor samples were homogenized. Then, the phage bound to the tumor mass or control organs were rescued by adding 0.5 ml ER2738 bacterial for 30 minutes at 37° C. The eluted phage particles were titered on agar plates in the presence of 1 mg/L of IPTG/X-Gal. In peptide competitive inhibition experiments, the phages were co-injected with 100 µg of synthetic peptide. We also used the control peptide. The organs and tumor masses were fixed in Bouin's solution for 2 h. After fixation, the samples were embedded in paraffin blocks. The paraffin sections were deparaffinized, rehydrated and subjected to immunostaining using M13 monoclonal antibody, as mentioned above.

We determined the titers of the phages in tumor mass and normal control organs (brain, lung, and heart). PC5-2 showed specific homing to tumor mass at concentrations 4 to 13-fold higher than control organs, including brain, heart and lung (FIG. 4A). Control helper phage did not show any specific targeting to tumor tissues (FIG. 4A). The tumor-homing ability of PC5-2 was further confirmed by a peptide competitive inhibition experiment, in which co-injection of synthetic peptide SP5-2 with PC5-2 markedly inhibited the recovery of phages from tumor mass (FIG. 4B). One hundred micrograms of SP5-2 inhibited 92% of PC5-2 binding to tumor mass, but the same concentration of the control peptide (Con-P) had no such inhibitory effect (FIG. 4B).

The tissue distribution of PC5-2 was also studied by immunostaining. SCID mice bearing NSCLC xenografts were injected i.v. with PC5-2 and the xenograft and control organs were removed and fixed for localization of the phage-binding site. The results showed that PC5-2 was localized in the tumor tissues (FIG. 4C, d). At a higher magnification, the immunoreactivity of anti-phage was seen on the plasma membrane with some diffusion in the surrounding cytoplasm of tumor cells (FIG. 4C, e). There was no reaction product on normal organs, such as brain, heart and, lung tissues (FIG. 4C, a-c), or on control phage treated tumor tissues (FIG. 4C, i). The specific targeting ability of PC5-2 with NSCLC xenograft was inhibited by the synthetic peptide SP5-2 in the in vivo homing experiment (FIG. 4C, j). Scale bar: 25 µm.

Example 5

Treatment of SCID Mice Bearing Human lung Cancer Xenografts with SP5-2-Lipo-Vin and SP5-2-Lipo-Dox The current standard chemotherapy for elderly patients with advanced NSCLC is the use of vinorelbine for single-agent chemotherapy (Kelly et al., 2001). To determine whether the lung cancer-homing peptide, SP5-2, could be used to improve the chemotherapeutic efficacy of cancer treatment, we coupled the peptide to liposome containing vinorelbine (SP5-2-Lipo-Vin). Peptide was coupled to NHS-PEG-DSPE [N-hydroxysuccinimido-carboxyl-polyethylene glycol (PEG; average molecular weight, 3000)-derived distearoylphosphatidylethanolamine (NOF Corporation, Tokyo, Japan)] at a 1:1.5 molar ratio. This coupling was done using the unique free amine group in the N-terminus of the peptide to produce peptidyl-PEG-DSPE. The reaction was completed and confirmed by quantitation of the remaining amino groups. The amino groups were measured with TNBS (Trinitrobenzenesulfonate) reagent (Habeeb AFSA, 1966). Liposomes composed of DSPC (distearoylphosphatidylcholine), Cholesterol, PEG-DSPE were hydrated at 55° C. in ammonium sulfate solution (250 mM $(NH_4)_2SO_4$, pH=5.0, 530 mOs) and extruded through polycarbonate membrane filters (Costar, Cambridge, Mass., USA) of 0.1 µm and 0.05 µm pore size using high-pressure extrusion equipment (Lipex Biomembranes, Vancouver, BC, Canada) at 60° C.; and anti-cancer drugs vinorelbine or doxorubicin were encapsulated in the liposomes by a remote loading method at a concentration of 1 mg drug per 10 µmol phospholipid. The final concentration of liposomes was determined by phosphate assay. After adding 1 ml acidic isopropanol (81 mM HCl) to 0.2 ml diluted drug-loaded liposomes, the amount of doxorubicin trapped inside the liposomes was determined with a spectrofluorometer (Hitachi F-4500, Hitachi, Ltd, Tokyo, Japan) using 470 nm as excitation wavelength and 582 nm as emission wavelength. Vesicle sizes were measured by dynamic laser scattering with a submicron particle analyzer (model N4 plus; Coulter Electronics, Hialeah, Fla., USA). Peptidyl-PEG-DSPE was transferred to pre-formed liposomes after co-incubation at temperature above the transition temperature of lipid bilayer (Zalipsky et al., 1997). There were 300-500 peptide molecules per liposome, computed as described previously (Kirpotin et al., 1997).

Mice 4-6 weeks of age were injected s.c. into the dorsolateral flank with human NSCLC cancer cells. Mice with size-matched tumors (tumor sizes about 50~100 $mm^3$) were randomly assigned to different treatment groups and treated with SP5-2-cojugated liposomes containing vinorelbine (SP5-2-Lipo-Vin) or doxorubicin (SP5-2-Lipo-Dox), and Lipo-Vin or Lipo-Dox through the tail vein. The mice were treated with the drug eight times (1 mg/kg, twice a week). The mouse body weights and the tumor sizes were measured twice a week with calipers. The tumor volumes were calculated using the equation: length×(width)$^2$×0.52. The differences in mean tumor volume were evaluated by ANOVA.

SCID mice bearing size-matched NSCLC xenograft (~100 $mm^3$) were treated with SP5-2-Lipo-Vin, Lipo-Vin and PBS separately through i.v. injection at a total vinorelbine dose of 48 mg/kg (12 times, 2 mg/kg twice a week).

The group of tumor-bearing mice that received the SP5-2-Lipo-Vin (FIG. 5A, Group a) were found to have significantly smaller-sized tumors than that of the Lipo-Vin and PBS groups (P<0.005) (FIG. 5A, Group b and Group c). The tumors of the Lipo-Vin (LV) group were found to have increased size to 6.75-fold larger than those in of the SP5-2-Lipo-Vin (SP5-2-LV) group. The tumors of the mice in the control PBS group were found to have increased size to 25-fold larger than those in SP5-2-Lipo-Vin group (n=6; *P<0.01) (FIG. 5A).

To assess the possible side effect caused by chemotherapeutic drugs, mice were weighed twice a week. The data revealed that the body weight change of the SP5-2-Lipo-Vin treated group (increased 1.37 g) was similar to the weight change of the PBS group (increased 1.33 g). In contrast, the Lipo-Vin treated group showed less increase in body weight (only increased 0.58 g) (n=6; *p<0.05) (FIG. 5B).

To further characterize the therapeutic efficacy of the targeting liposome, we compared the animal survival rate after treatment with SP5-2-Lipo-Vin, Lipo-Vin or PBS separately for 102 days. All animals died in the PBS treated group (survival rate 0%). Three animals died in the Lipo-Vin treated group (survival rate 40%), while the SP5-2-Lipo-Vin treated group showed a significantly increased survival rate of 80% when the experiment was finished at day 102 (n=5; FIG. 5C).

To further test whether SP5-2 could increase the therapeutic efficacy for lung cancer, we linked this targeting ligand to another anti-cancer drug, doxorubicin (SP5-2-Lipo-Dox), to treat another NSCLC, H460. Doxorubicin is one of the most frequently used anticancer drugs. In addition to its cytotoxic effect on cancer cells, this chemotherapeutic agent is known to have antiangiogenic activity (Arap et al., 1998). The data showed that SP5-2-Lipo-Dox (SP5-2-LD) also has higher therapeutic efficiency than Lipo-Dox (LD) (n=6*p<0.05) (FIG. 5D). The targeting liposome SP5-2-Lipo-Dox markedly inhibited the H460-derived tumor growth compared to the mice treated with PBS (FIG. 5D). These results indicated that conjugation of Lipo-Vin or Lipo-Dox with targeting ligand SP5-2 enhanced the efficacy of the drugs to inhibit human lung cancer xenografts in animal models.

TABLE 1

Alignment of phage-displayed peptide sequences selected by NSCLC cells.

| Phage clone | Phage-displayed peptide sequence | $^a$Frequency |
|---|---|---|
| PC5-2 | TDSILRSYDWTY | 27/30 (SEQ ID NO: 2) |
| PC5-4 | DMPKQLLAPWYY | 3/30 (SEQ ID NO: 4) |

TABLE 1-continued

Alignment of phage-displayed peptide sequences selected by NSCLC cells.

| Phage clone | Phage-displayed peptide sequence | $^a$Frequency |
|---|---|---|
| PC4-1 | TDSILRSYDWTY | 20/23 (SEQ ID NO: 6) |
| PC4-5 | DMPKQLLAPWYY | 2/23 (SEQ ID NO: 8) |
| PC4-9 | SYPLSFLGPLIS | 1/23 (SEQ ID NO: 10) |
| PC3-1 | TDSILRSYDWTY | 1/5 (SEQ ID NO: 12) |
| PC3-2 | TQQPLEGHQLPY | 1/5 (SEQ ID NO: 14) |
| PC3-3 | TGVSWSVAQPSF | 1/5 (SEQ ID NO: 16) |
| PC3-4 | SVSVGMKPSPRP | 1/5 (SEQ ID NO: 18) |
| PC3-5 | SQWNSPPSSAAF | 1/5 (SEQ ID NO: 20) |

$^a$Phage-displayed consensus amino acid sequences are shown in boldface.
PC3-1, PC4-1 and PC5-2 display the same amino acid sequence.
PC4-5 and PC5-4 display the same amino acid sequence.

The invention claimed is:

1. A peptide comprising a variant of SEQ ID NO: 2, wherein the variant comprises consecutive amino acids S-Y-D-W-T-Y.

2. A fusion peptide comprising a first peptide fused to a second peptide, wherein the first peptide comprises the peptide of claim 1.

3. The fusion peptide of claim 2, wherein the second peptide comprises an epitope.

4. The peptide of claim 1, wherein the peptide comprises one more or more labels.

5. The peptide of claim 4, wherein the label is chosen from FITC, biotin, and a radioisotope.

6. The peptide of claim 1, wherein the peptide is conjugated to one or more drugs chosen from doxorubicin, vinorelbine, an oligonucleotide, a toxin, an anti-VEGF aptamer, and a radioactive molecule.

7. A liposome comprising the peptide of claim 1.

8. The liposome of claim 7, wherein the peptide is encoded by a variant of SEQ ID NO: 1 that hybridizes under stringent conditions to the complement of SEQ ID NO: 1.

9. The liposome of claim 7, wherein the liposome further comprises at least one drug chosen from doxorubicin, vinorelbine, an oligonucleotide, a toxin, an anti-VEGF aptamer, and a radioactive molecule.

10. The liposome of claim 9, wherein the drug comprises doxorubicin.

11. The liposome of claim 9, wherein the drug comprises vinorelbine.

12. The liposome of claim 9, wherein said liposome comprises a pharmaceutically acceptable carrier.

13. A peptide encoded by a polynucleotide comprising a variant of SEQ ID NO: 1 that hybridizes under stringent conditions to the complement of SEQ ID NO: 1 and encodes a polypeptide comprising consecutive amino acids S-Y-D-W-T-Y.

* * * * *

SEQUENCE LISTING

<160> NUMBER OF SEQ ID NOS: 22

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
actgattcta ttctgcggag ttatgattgg acttat                               36

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Asp Ser Ile Leu Arg Ser Tyr Asp Trp Thr Tyr
 1               5                  10

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gatatgccta agcagctgtt ggcgccttgg tattat                               36

<210> SEQ ID NO 4
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 4

Asp Met Pro Lys Gln Leu Leu Ala Pro Trp Tyr Tyr
 1               5                  10

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
actgattcta ttctgcggag ttatgattgg acttat                                 36

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Thr Asp Ser Ile Leu Arg Ser Tyr Asp Trp Thr Tyr
 1               5                  10

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatatgccta agcagctgtt ggcgccttgg tattat                                 36

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Met Pro Lys Gln Leu Leu Ala Pro Trp Tyr Tyr
 1               5                  10

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
agttatcctc tttcgttttt gggtcctctg atttcg                                 36

<210> SEQ ID NO 10
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 10

Ser Tyr Pro Leu Ser Phe Leu Gly Pro Leu Ile Ser
 1               5                  10

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
actgattcta ttctgcggag ttatgattgg acttat                           36

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Thr Asp Ser Ile Leu Arg Ser Tyr Asp Trp Thr Tyr
 1               5                  10

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
actcagcagc ctctggaagg tcatcagctg ccttat                           36

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Thr Gln Gln Pro Leu Glu Gly His Gln Leu Pro Tyr
 1               5                  10

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
actggtgttt cttggtctgt ggctcagcct tctttt                           36

<210> SEQ ID NO 16
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Gly Val Ser Trp Ser Val Ala Gln Pro Ser Phe
 1               5                  10

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tctgtttctg tgggtatgaa gccgagtcct aggcct                           36

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Val Ser Val Gly Met Lys Pro Ser Pro Arg Pro
 1               5                  10

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tctcagtgga attctcctcc ttcttctgct gctttt                           36

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ser Gln Trp Asn Ser Pro Pro Ser Ser Ala Ala Phe
 1               5                  10

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ccctcatagt tagcgtaacg                                             20

<210> SEQ ID NO 22
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Leu Leu Asp Thr Asn Arg Pro Leu Leu Pro Tyr
 1               5                  10
```